(12) United States Patent
Chen

(10) Patent No.: US 11,382,986 B2
(45) Date of Patent: Jul. 12, 2022

(54) COMPOSITIONS AND METHODS TO EXPEDITE ANTIBODY-BASED EXCHANGE IMAGING

(71) Applicant: Ultivue, Inc., Cambridge, MA (US)

(72) Inventor: Xi Chen, West Newton, MA (US)

(73) Assignee: ULTIVUE, INC., Cambridge, MA (US)

( * ) Notice: Subject to any disclaimer, the term of this patent is extended or adjusted under 35 U.S.C. 154(b) by 214 days.

(21) Appl. No.: 16/129,895

(22) Filed: Sep. 13, 2018

(65) Prior Publication Data

US 2019/0000988 A1    Jan. 3, 2019

Related U.S. Application Data

(63) Continuation of application No. PCT/US2017/035375, filed on Jun. 1, 2017.
(Continued)

(51) Int. Cl.
*A61K 47/68*     (2017.01)
*C07K 16/42*     (2006.01)
(Continued)

(52) U.S. Cl.
CPC ...... *A61K 47/6873* (2017.08); *A61K 47/6849* (2017.08); *C07K 16/12* (2013.01); *C07K 16/42* (2013.01); *G01N 33/536* (2013.01); *G01N 33/58* (2013.01); *G01N 33/6854* (2013.01); *C07K 2317/30* (2013.01); *C07K 2317/55* (2013.01)

(58) Field of Classification Search
CPC ............ A61K 47/6873; A61K 47/6849; C07K 16/12; C07K 16/42; C07K 2317/30; C07K 2317/55; G01N 33/536; G01N 33/58; G01N 33/6854
See application file for complete search history.

(56) References Cited

U.S. PATENT DOCUMENTS 8,323,903 B2    12/2012  Archer et al.
9,944,972 B2 *   4/2018  Yin ...................... C12Q 1/6818
(Continued)

FOREIGN PATENT DOCUMENTS

WO   WO2014028538 A2 *  2/2014
WO       2015017586 A1    2/2015

OTHER PUBLICATIONS

Abboud et al., Directed Selection and Characterization of High-affinity Synergistic Antibodies, Dissertation (online), Tulane University School of Medicine, Oct. 2007, p. 33, 1st paragraph.
(Continued)

*Primary Examiner* — Tracy Vivlemore
*Assistant Examiner* — Nam P Nguyen
(74) *Attorney, Agent, or Firm* — McNeill Baur PLLC

(57) ABSTRACT

A method for exchange imaging of at least two targets in a sample includes (a) incubating a sample with at least two or more target-recognizing antibodies, each bound to a corresponding monovalent tight antibody binder-docketing moiety (MTAB-DM) reagent capable of binding monovalently to the target-recognizing antibodies, (b) applying at least two imager moieties corresponding to the MTAB-DM, either in series, in batches, or in parallel, and (d) imaging the at least two imager moieties either in series, in batches, or in parallel.

16 Claims, 6 Drawing Sheets

Specification includes a Sequence Listing.

Related U.S. Application Data

(60) Provisional application No. 62/344,441, filed on Jun. 2, 2016.

(51) Int. Cl.
| | | |
|---|---|---|
| *G01N 33/536* | (2006.01) | |
| *G01N 33/58* | (2006.01) | |
| *C07K 16/12* | (2006.01) | |
| *G01N 33/68* | (2006.01) | |

(56) References Cited

U.S. PATENT DOCUMENTS

| 10,190,151 B2* | 1/2019 | Yin | C12Q 1/6804 |
|---|---|---|---|
| 10,294,510 B2* | 5/2019 | Yin | C12Q 1/6804 |
| 2003/0073149 A1* | 4/2003 | Archer | B82Y 30/00 |
| | | | 435/7.92 |
| 2017/0038391 A1 | 2/2017 | Gutierrez et al. | |
| 2018/0371532 A1* | 12/2018 | Chen | C12Q 1/6804 |
| 2019/0323061 A1* | 10/2019 | Yin | C12Q 1/6804 |

OTHER PUBLICATIONS

Agasti et al., DNA-barcoded labeling probes for highly multiplexed Exchange-PAINT imaging, Chem. Sci. 2017, 8, 3080-3091.

Crivianu-Gaita et al. High efficiency reduction capability for the formation of Fab' antibody fragments from F(ab)2 units, Biochemistry and Biophysics Reports 2 (2015) 23-28.

Graille et al., Crystal structure of a *Staphylococcus aureus* protein A domain complexed with the Fab fragment of a human IgM antibody: Structural basis for recognition of B-cell receptors and superantigen activity, PNAS, 97 (10):5399-5404, 2000.

Hermanson et al., Antibody Modification and Conjugation, Bioconjugate Techniques 3rd. Ed., chapter 20, 867-920 (2013).

Hermanson et al., Functional Targets for Bioconjugation, Bioconjugate Techniques 3rd. Ed., chapter 2, 127-228 (2013).

International Search Report and Written Opinion issued in PCT/US2017/035375, dated Aug. 31, 2017, 15 pages.

Jungmann et al., Multiplexed 3D Cellular Super-Resolution Imaging with DNA-PAINT and Exchange-PAINT, Nat Methods, Mar. 2014, 11(3):313-318.

Kastern et al., Structure of Peptostreptococcal Protein L and Identification of a Repeated Immunoglobulin Light Chain-binding Domain, The Journal of Biological Chemistry, 267(18):12820-12825, 1992.

Owen et al., A Reproducible Technique for Specific Labeling of Antigens Using Preformed Fluorescent Molecular IgG-F(ab')2 Complexes From Primary Antibodies of the Same Species, Microsc. Res. Tech. Jun. 2010, 73(6):623-630.

Sjöbring et al., Streptococcal Protein G, The Journal of Biological Chemistry, 266(1):399-405, 1991.

Wang et al., Rapid sequential in situ multiplexing with DNA-Exchange-Imaging, Cold Spring Harbor Laboratory, Mar. 2017, pp. 1-15.

* cited by examiner

SEQUENCE LISTING

```
<160> NUMBER OF SEQ ID NOS: 13

<210> SEQ ID NO 1
<211> LENGTH: 12
<212> TYPE: DNA
<213> ORGANISM: Artificial Sequence
<220> FEATURE:
<223> OTHER INFORMATION: Docking moiety1

<400> SEQUENCE: 1
ttgccacctt cg                                                        12

<210> SEQ ID NO 2
<211> LENGTH: 12
<212> TYPE: DNA
<213> ORGANISM: Artificial Sequence
<220> FEATURE:
```

<223> OTHER INFORMATION: Docking moiety2

<400> SEQUENCE: 2
taacggtcaa gc                                                              12

<210> SEQ ID NO 3
<211> LENGTH: 12
<212> TYPE: DNA
<213> ORGANISM: Artificial Sequence
<220> FEATURE:
<223> OTHER INFORMATION: Docking moiety3

<400> SEQUENCE: 3
cgtagccctg ac                                                              12

<210> SEQ ID NO 4
<211> LENGTH: 12
<212> TYPE: DNA
<213> ORGANISM: Artificial Sequence
<220> FEATURE:
<223> OTHER INFORMATION: Docking moiety4

<400> SEQUENCE: 4
tgctgcctct tt                                                              12

<210> SEQ ID NO 5
<211> LENGTH: 12
<212> TYPE: DNA
<213> ORGANISM: Artificial Sequence
<220> FEATURE:
<223> OTHER INFORMATION: Imager moiety1

<400> SEQUENCE: 5
cgaaggtggc aa                                                              12

<210> SEQ ID NO 6
<211> LENGTH: 12
<212> TYPE: DNA
<213> ORGANISM: Artificial Sequence
<220> FEATURE:
<223> OTHER INFORMATION: Imager moiety2

<400> SEQUENCE: 6
gcttgaccgt ta                                                              12

<210> SEQ ID NO 7
<211> LENGTH: 12
<212> TYPE: DNA
<213> ORGANISM: Artificial Sequence
<220> FEATURE:
<223> OTHER INFORMATION: Imager moiety3

<400> SEQUENCE: 7
gtcagggcta cg                                                              12

<210> SEQ ID NO 8
<211> LENGTH: 12
<212> TYPE: DNA
<213> ORGANISM: Artificial Sequence
<220> FEATURE:
<223> OTHER INFORMATION: Imager moiety4

<400> SEQUENCE: 8
aaagaggcag ca                                                              12

```
<210> SEQ ID NO 9
<211> LENGTH: 508
<212> TYPE: PRT
<213> ORGANISM: Staphylococcus aureus

<400> SEQUENCE: 9

Met Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
                20                  25                  30

Ala Ala Asn Ala Ala Gln His Asp Glu Ala Gln Gln Asn Ala Phe Tyr
            35                  40                  45

Gln Val Leu Asn Met Pro Asn Leu Asn Ala Asp Gln Arg Asn Gly Phe
50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Lys Phe Asn Lys Asp Gln Gln Ser Ala Phe Tyr Glu Ile Leu
            100                 105                 110

Asn Met Pro Asn Leu Asn Glu Glu Gln Arg Asn Gly Phe Ile Gln Ser
        115                 120                 125

Leu Lys Asp Asp Pro Ser Gln Ser Thr Asn Val Leu Gly Glu Ala Lys
130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ala Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
                325                 330                 335

Glu Asp Gly Asn Lys Pro Gly Lys Glu Asp Gly Asn Lys Pro Gly Lys
            340                 345                 350

Glu Asp Asn Lys Lys Pro Gly Lys Glu Asp Gly Asn Lys Pro Gly Lys
        355                 360                 365

Glu Asp Asn Lys Lys Pro Gly Lys Glu Asp Gly Asn Lys Pro Gly Lys
    370                 375                 380
```

```
Glu Asp Gly Asn Lys Pro Gly Lys Glu Asp Gly Asn Lys Pro Gly Lys
385                 390                 395                 400

Glu Asp Gly Asn Lys Pro Gly Lys Glu Asp Gly Asn Gly Val His Val
                405                 410                 415

Val Lys Pro Gly Asp Thr Val Asn Asp Ile Ala Lys Ala Asn Gly Thr
            420                 425                 430

Thr Ala Asp Lys Ile Ala Ala Asp Asn Lys Leu Ala Asp Lys Asn Met
        435                 440                 445

Ile Lys Pro Gly Gln Glu Leu Val Val Asp Lys Lys Gln Pro Ala Asn
    450                 455                 460

His Ala Asp Ala Asn Lys Ala Gln Ala Leu Pro Glu Thr Gly Glu Glu
465                 470                 475                 480

Asn Pro Phe Ile Gly Thr Thr Val Phe Gly Gly Leu Ser Leu Ala Leu
                485                 490                 495

Gly Ala Ala Leu Leu Ala Gly Arg Arg Arg Glu Leu
            500                 505

<210> SEQ ID NO 10
<211> LENGTH: 593
<212> TYPE: PRT
<213> ORGANISM: Streptococcus sp. group G

<400> SEQUENCE: 10

Met Glu Lys Glu Lys Lys Val Lys Tyr Phe Leu Arg Lys Ser Ala Phe
1               5                   10                  15

Gly Leu Ala Ser Val Ser Ala Ala Phe Leu Val Gly Ser Thr Val Phe
            20                  25                  30

Ala Val Asp Ser Pro Ile Glu Asp Thr Pro Ile Ile Arg Asn Gly Gly
        35                  40                  45

Glu Leu Thr Asn Leu Leu Gly Asn Ser Glu Thr Thr Leu Ala Leu Arg
    50                  55                  60

Asn Glu Glu Ser Ala Thr Ala Asp Leu Thr Ala Ala Val Ala Asp
65                  70                  75                  80

Thr Val Ala Ala Ala Ala Glu Asn Ala Gly Ala Ala Ala Trp Glu
                85                  90                  95

Ala Ala Ala Ala Asp Ala Leu Ala Lys Ala Lys Ala Asp Ala Leu
            100                 105                 110

Lys Glu Phe Asn Lys Tyr Gly Val Ser Asp Tyr Tyr Lys Asn Leu Ile
        115                 120                 125

Asn Asn Ala Lys Thr Val Glu Gly Val Lys Asp Leu Gln Ala Gln Val
    130                 135                 140

Val Glu Ser Ala Lys Lys Ala Arg Ile Ser Glu Ala Thr Asp Gly Leu
145                 150                 155                 160

Ser Asp Phe Leu Lys Ser Gln Thr Pro Ala Glu Asp Thr Val Lys Ser
                165                 170                 175

Ile Glu Leu Ala Glu Ala Lys Val Leu Ala Asn Arg Glu Leu Asp Lys
            180                 185                 190

Tyr Gly Val Ser Asp Tyr His Lys Asn Leu Ile Asn Asn Ala Lys Thr
        195                 200                 205

Val Glu Gly Val Lys Asp Leu Gln Ala Gln Val Val Glu Ser Ala Lys
    210                 215                 220

Lys Ala Arg Ile Ser Glu Ala Thr Asp Gly Leu Ser Asp Phe Leu Lys
225                 230                 235                 240

Ser Gln Thr Pro Ala Glu Asp Thr Val Lys Ser Ile Glu Leu Ala Glu
                245                 250                 255
```

Ala Lys Val Leu Ala Asn Arg Glu Leu Asp Lys Tyr Gly Val Ser Asp
            260                 265                 270

Tyr Tyr Lys Asn Leu Ile Asn Asn Ala Lys Thr Val Glu Gly Val Lys
        275                 280                 285

Ala Leu Ile Asp Glu Ile Leu Ala Ala Leu Pro Lys Thr Asp Thr Tyr
    290                 295                 300

Lys Leu Ile Leu Asn Gly Lys Thr Leu Lys Gly Glu Thr Thr Thr Glu
305                 310                 315                 320

Ala Val Asp Ala Ala Thr Ala Glu Lys Val Phe Lys Gln Tyr Ala Asn
                325                 330                 335

Asp Asn Gly Val Asp Gly Glu Trp Thr Tyr Asp Ala Thr Lys Thr
            340                 345                 350

Phe Thr Val Thr Glu Lys Pro Glu Val Ile Asp Ala Ser Glu Leu Thr
        355                 360                 365

Pro Ala Val Thr Thr Tyr Lys Leu Val Ile Asn Gly Lys Thr Leu Lys
    370                 375                 380

Gly Glu Thr Thr Thr Glu Ala Val Asp Ala Ala Thr Ala Glu Lys Val
385                 390                 395                 400

Phe Lys Gln Tyr Ala Asn Asp Asn Gly Val Asp Gly Glu Trp Thr Tyr
                405                 410                 415

Asp Asp Ala Thr Lys Thr Phe Thr Val Thr Glu Lys Pro Glu Val Ile
            420                 425                 430

Asp Ala Ser Glu Leu Thr Pro Ala Val Thr Thr Tyr Lys Leu Val Ile
        435                 440                 445

Asn Gly Lys Thr Leu Lys Gly Glu Thr Thr Thr Lys Ala Val Asp Ala
    450                 455                 460

Glu Thr Ala Glu Lys Ala Phe Lys Gln Tyr Ala Asn Asp Asn Gly Val
465                 470                 475                 480

Asp Gly Val Trp Thr Tyr Asp Asp Ala Thr Lys Thr Phe Thr Val Thr
                485                 490                 495

Glu Met Val Thr Glu Val Pro Gly Asp Ala Pro Thr Glu Pro Glu Lys
            500                 505                 510

Pro Glu Ala Ser Ile Pro Leu Val Pro Leu Thr Pro Ala Thr Pro Ile
        515                 520                 525

Ala Lys Asp Asp Ala Lys Lys Asp Asp Thr Lys Lys Glu Asp Ala Lys
    530                 535                 540

Lys Pro Glu Ala Lys Lys Glu Asp Ala Lys Lys Ala Glu Thr Leu Pro
545                 550                 555                 560

Thr Thr Gly Glu Gly Ser Asn Pro Phe Phe Thr Ala Ala Ala Leu Ala
                565                 570                 575

Val Met Ala Gly Ala Gly Ala Leu Ala Val Ala Ser Lys Arg Lys Glu
            580                 585                 590

Asp

<210> SEQ ID NO 11
<211> LENGTH: 992
<212> TYPE: PRT
<213> ORGANISM: Peptostreptococcus magnus

<400> SEQUENCE: 11

Met Lys Ile Asn Lys Lys Leu Leu Met Ala Ala Leu Ala Gly Ala Ile
1               5                   10                  15

Val Val Gly Gly Gly Ala Asn Ala Tyr Ala Ala Glu Glu Asp Asn Thr
            20                  25                  30

```
Asp Asn Asn Leu Ser Met Asp Glu Ile Ser Asp Ala Tyr Phe Asp Tyr
            35                  40                  45

His Gly Asp Val Ser Asp Ser Val Asp Pro Val Glu Glu Glu Ile Asp
        50                  55                  60

Glu Ala Leu Ala Lys Ala Leu Ala Glu Ala Lys Glu Thr Ala Lys Lys
 65                  70                  75                  80

His Ile Asp Ser Leu Asn His Leu Ser Glu Thr Ala Lys Lys Leu Ala
                85                  90                  95

Lys Asn Asp Ile Asp Ser Ala Thr Thr Ile Asn Ala Ile Asn Asp Ile
                100                 105                 110

Val Ala Arg Ala Asp Val Met Glu Arg Lys Thr Ala Glu Lys Glu Glu
            115                 120                 125

Ala Glu Lys Leu Ala Ala Ala Lys Glu Thr Ala Lys Lys His Ile Asp
        130                 135                 140

Glu Leu Lys His Leu Ala Asp Lys Thr Lys Glu Leu Ala Lys Arg Asp
145                 150                 155                 160

Ile Asp Ser Ala Thr Thr Ile Asn Ala Ile Asn Asp Ile Val Ala Arg
                165                 170                 175

Ala Asp Val Met Glu Arg Lys Thr Ala Glu Lys Glu Glu Ala Glu Lys
            180                 185                 190

Leu Ala Ala Ala Lys Glu Thr Ala Lys Lys His Ile Asp Glu Leu Lys
        195                 200                 205

His Leu Ala Asp Lys Thr Lys Glu Leu Ala Lys Arg Asp Ile Asp Ser
    210                 215                 220

Ala Thr Thr Ile Asp Ala Ile Asn Asp Ile Val Ala Arg Ala Asp Val
225                 230                 235                 240

Met Glu Arg Lys Leu Ser Glu Lys Glu Thr Pro Glu Pro Glu Glu Glu
            245                 250                 255

Val Thr Ile Lys Ala Asn Leu Ile Phe Ala Asp Gly Ser Thr Gln Asn
            260                 265                 270

Ala Glu Phe Lys Gly Thr Phe Ala Lys Ala Val Ser Asp Ala Tyr Ala
        275                 280                 285

Tyr Ala Asp Ala Leu Lys Lys Asp Asn Gly Glu Tyr Thr Val Asp Val
    290                 295                 300

Ala Asp Lys Gly Leu Thr Leu Asn Ile Lys Phe Ala Gly Lys Lys Glu
305                 310                 315                 320

Lys Pro Glu Glu Pro Lys Glu Glu Val Thr Ile Lys Val Asn Leu Ile
            325                 330                 335

Phe Ala Asp Gly Lys Thr Gln Thr Ala Glu Phe Lys Gly Thr Phe Glu
        340                 345                 350

Glu Ala Thr Ala Lys Ala Tyr Ala Tyr Ala Asp Leu Leu Ala Lys Glu
    355                 360                 365

Asn Gly Glu Tyr Thr Ala Asp Leu Glu Asp Gly Gly Asn Thr Ile Asn
370                 375                 380

Ile Lys Phe Ala Gly Lys Glu Thr Pro Glu Thr Pro Glu Glu Pro Lys
            385                 390                 395                 400

Glu Glu Val Thr Ile Lys Val Asn Leu Ile Phe Ala Asp Gly Lys Ile
            405                 410                 415

Gln Thr Ala Glu Phe Lys Gly Thr Phe Glu Glu Ala Thr Ala Lys Ala
        420                 425                 430

Tyr Ala Tyr Ala Asn Leu Leu Ala Lys Glu Asn Gly Glu Tyr Thr Ala
    435                 440                 445
```

```
Asp Leu Glu Asp Gly Gly Asn Thr Ile Asn Ile Lys Phe Ala Gly Lys
    450                 455                 460

Glu Thr Pro Glu Thr Pro Glu Pro Lys Glu Glu Val Thr Ile Lys
465                 470                 475                 480

Val Asn Leu Ile Phe Ala Asp Gly Lys Thr Gln Thr Ala Glu Phe Lys
                    485                 490                 495

Gly Thr Phe Glu Glu Ala Thr Ala Glu Ala Tyr Arg Tyr Ala Asp Leu
                500                 505                 510

Leu Ala Lys Val Asn Gly Glu Tyr Thr Ala Asp Leu Glu Asp Gly Gly
            515                 520                 525

Tyr Thr Ile Asn Ile Lys Phe Ala Gly Lys Glu Gln Pro Gly Glu Asn
530                 535                 540

Pro Gly Ile Thr Ile Asp Glu Trp Leu Leu Lys Asn Ala Lys Glu Glu
545                 550                 555                 560

Ala Ile Lys Glu Leu Lys Glu Ala Gly Ile Thr Ser Asp Leu Tyr Phe
                565                 570                 575

Ser Leu Ile Asn Lys Ala Lys Thr Val Glu Gly Val Glu Ala Leu Lys
                580                 585                 590

Asn Glu Ile Leu Lys Ala His Ala Gly Glu Glu Thr Pro Glu Leu Lys
            595                 600                 605

Asp Gly Tyr Ala Thr Tyr Glu Glu Ala Glu Ala Ala Lys Glu Ala
        610                 615                 620

Leu Lys Asn Asp Asp Val Asn Asn Ala Tyr Glu Ile Val Gln Gly Ala
625                 630                 635                 640

Asp Gly Arg Tyr Tyr Val Leu Lys Ile Glu Val Ala Asp Glu Glu
                645                 650                 655

Glu Pro Gly Glu Asp Thr Pro Glu Val Gln Glu Gly Tyr Ala Thr Tyr
                660                 665                 670

Glu Glu Ala Glu Ala Ala Ala Lys Glu Ala Leu Lys Glu Asp Lys Val
            675                 680                 685

Asn Asn Ala Tyr Glu Val Val Gln Gly Ala Asp Gly Arg Tyr Tyr Tyr
        690                 695                 700

Val Leu Lys Ile Glu Asp Lys Glu Asp Glu Gln Pro Gly Glu Glu Pro
705                 710                 715                 720

Gly Glu Asn Pro Gly Ile Thr Ile Asp Glu Trp Leu Leu Lys Asn Ala
                725                 730                 735

Lys Glu Asp Ala Ile Lys Glu Leu Lys Glu Ala Gly Ile Ser Ser Asp
                740                 745                 750

Ile Tyr Phe Asp Ala Ile Asn Lys Ala Lys Thr Val Glu Gly Val Glu
            755                 760                 765

Ala Leu Lys Asn Glu Ile Leu Lys Ala His Ala Glu Lys Pro Gly Glu
770                 775                 780

Asn Pro Gly Ile Thr Ile Asp Glu Trp Leu Leu Lys Asn Ala Lys Glu
785                 790                 795                 800

Ala Ala Ile Lys Glu Leu Lys Glu Ala Gly Ile Thr Ala Glu Tyr Leu
                805                 810                 815

Phe Asn Leu Ile Asn Lys Ala Lys Thr Val Glu Gly Val Glu Ser Leu
                820                 825                 830

Lys Asn Glu Ile Leu Lys Ala His Ala Glu Lys Pro Gly Glu Asn Pro
            835                 840                 845

Gly Ile Thr Ile Asp Glu Trp Leu Leu Lys Asn Ala Lys Glu Asp Ala
850                 855                 860

Ile Lys Glu Leu Lys Glu Ala Gly Ile Thr Ser Asp Ile Tyr Phe Asp
```

```
                865                 870                 875                 880
Ala Ile Asn Lys Ala Lys Thr Ile Glu Gly Val Glu Ala Leu Lys Asn
                    885                 890                 895

Glu Ile Leu Lys Ala His Lys Lys Asp Glu Glu Pro Gly Lys Lys Pro
                    900                 905                 910

Gly Glu Asp Lys Lys Pro Glu Asp Lys Lys Pro Gly Glu Asp Lys Lys
                    915                 920                 925

Pro Glu Asp Lys Lys Pro Gly Glu Asp Lys Lys Pro Glu Asp Lys Lys
            930                 935                 940

Pro Gly Lys Thr Asp Lys Asp Ser Pro Asn Lys Lys Lys Ala Lys
945                 950                 955                 960

Leu Pro Lys Ala Gly Ser Glu Ala Glu Ile Leu Thr Leu Ala Ala Ala
                    965                 970                 975

Ala Leu Ser Thr Ala Ala Gly Ala Tyr Val Ser Leu Lys Lys Arg Lys
                    980                 985                 990

<210> SEQ ID NO 12
<211> LENGTH: 23
<212> TYPE: DNA
<213> ORGANISM: Artificial Sequence
<220> FEATURE:
<223> OTHER INFORMATION: 5' ATTO488-labeled oligonucleotide

<400> SEQUENCE: 12
tctgctttcc cgttatacat cta                                                23

<210> SEQ ID NO 13
<211> LENGTH: 12
<212> TYPE: DNA
<213> ORGANISM: Artificial Sequence
<220> FEATURE:
<223> OTHER INFORMATION: Docking moiety

<400> SEQUENCE: 13
tctgctttcc cg                                                            12
```

COMPOSITIONS AND METHODS TO EXPEDITE ANTIBODY-BASED EXCHANGE IMAGING

CROSS-REFERENCE TO RELATED APPLICATIONS

This application is a continuation of International Application No. PCT/US17/35375 filed Jun. 1, 2017, which claims the benefit of priority of U.S. Provisional Application No. 62/344,441, filed Jun. 2, 2016, the contents of each of which are incorporated by reference herein in their entirety for any purpose.

SEQUENCE LISTING

A sequence listing is submitted concurrently with this application as an ASCII formatted text file via EFS-Web, with a file name of "2017-05-11_01168-0006-00PCT_SeqList_ST25.txt", a creation date of May 11, 2017, and a size of 20,200 bytes. The sequence listing filed via EFS-Web is part of the specification and is hereby incorporated by reference in its entirety.

DESCRIPTION

Field

This application provides for compositions and methods to expedite antibody-based exchange imaging.

Background

Super-resolution imaging can be used to detect multiple targets in a single sample. Previously a first antibody against a first target was used to label a first target in a sample, that label imaged, and the antibody or its label removed or destroyed before labeling the sample with a second antibody against a second target and so on. This approach, however, was very labor intensive and required long separate incubations with each antibody.

Exchange imaging provided some improvement to achieve multiplexing capability so that a number of targets can be imaged on the same sample. Exchange imaging can involve the following steps: (1) attaching different Decodable information-carrying molecules (called docking moieties, or DMs) to different target-recognizing molecules, respectively, (2) using a set of molecules (called imager moieties), each specifically recognizing a docking moiety and carrying an observable moiety, to label a subset of docking moieties, and imaging the corresponding subset of targets, (3) removing the set of imager moieties used in step 2 or inactivating the observable moieties on such imager moieties, and (4) using another set of imager moieties, each specifically recognizing a docking moiety and carrying an observable moiety, to label another subset of docking moieties, and imaging the corresponding subset of targets, and (5) optionally, steps 3 and 4 can be repeated to visualize multiple subsets of targets.

One non-limiting example of exchange imaging is DNA exchange immunofluorescence, where one uses antibodies as the target-recognizing molecules to image target proteins or other biomolecules, DNA oligonucleotides as docking moieties, and DNA oligonucleotides that are complementary to the docking moieties and labeled with observable moieties, such as fluorophores, as the imager moieties. In step 3, one may remove the DNA using high temperature, denaturant, DNA helicase, DNase, and/or strand displacement, or may remove the observable moiety, such as fluorophores, on the docking moieties by chemical cleavage, enzymatic cleavage, chemical bleaching, photo-bleaching, and/or photochemical bleaching.

In doing DNA exchange immunofluorescence, one practical challenge is attaching the docking moieties to the target-recognizing antibody (sometimes referred to as the primary antibody). One conventional and convenient, albeit limiting, method is to take advantage of full length secondary antibodies that can differentiate different primary antibodies. For example, in a 2-plex DNA exchange immunofluorescence, if the two primary antibodies are of two host species (e.g., one from mouse and the other from rabbit), one can use two premade secondary antibodies (one anti-mouse and the other anti-rabbit) that are attached to two distinct docking moieties. Similarly, if the antibodies are of different isotypes (e.g., IgG1, IgG2a, and IgG2b), isotype-specific secondary antibodies can be used. However, When multiple primary antibodies are of the same host species and isotypes, this strategy can no longer be used. Instead, one would usually attach the docking moieties directly to the target-recognizing antibodies before carrying out the staining Although a number of antibody conjugation methods exist (for example, see Greg T. Hermanson, Bioconjugate Techniques 3rd. Ed., chapters 2 and 20, ISBN: 978-0-12-382239-0 (2013)) most of them are undesirable for reasons such as having low yield, requiring large quantity of expensive primary antibody (which is likely monoclonal in nature), requiring primary of high purity, being labor intensive, or being expensive. Primary antibodies are also often sold in formulations including carrier proteins like albumin and such carrier proteins can interference with certain antibody conjugation techniques.

Therefore, the art requires improved methods for attaching docking moieties to primary antibodies for use in exchange imaging.

SUMMARY

In accordance with the description, in some embodiments a method for exchange imaging of at least two targets in a sample comprises (a) providing at least two or more target-recognizing antibodies, each bound to a corresponding MTAB-DM reagent capable of binding monovalently to the target-recognizing antibodies; (b) incubating a sample with the two or more target-recognizing antibodies, each bound to a corresponding MTAB-DM reagent; (c) applying at least two imager moieties corresponding to the MTAB-DM, either in series, in batches, or in parallel; (d) imaging the at least two imager moieties either in series, in batches, or in parallel.

In some embodiments, the MTAB comprises Protein A, Protein G, Protein A/G, Protein L, or a monovalent antibody fragment. In some embodiments, the DMs (docking moieties) and the imager moieties comprise nucleic acids. In some embodiments, all of the target-recognizing antibodies each bound to a corresponding MTAB-DM reagent are incubated with the sample simultaneously. In some embodiments, all of the imager moieties are applied in series and the imaging occurs in series. In some embodiments, all of the imager moieties are applied in parallel and the imaging occurs in parallel. In some embodiments, the imager moieties are applied in batches with at least one batch having two or more imager moieties and the method having at least two batches and wherein the imaging occurs in at least two batches. In some embodiments, each imager moiety is labeled with a different observable moiety. In some embodiments, each imager moiety is labeled with the same observable moiety. In some embodiments, some of the imager moieties are labeled with the same observable moiety and some of the imager moieties are labeled with different observable moieties. In some embodiments, before incubating the target-recognizing antibodies with the sample, an excess of MTAB-DM is employed to prevent an excess of free target-recognizing antibody. In some embodiments, before incubating the target-recognizing antibodies with the sample, free MTAB-DM is removed using ultrafiltration or gel filtration. In some embodiments, nonspecific antibody is added to the staining, washing, and/or imaging buffer. In some embodiments, the nonspecific antibody is an antibody from the same host species as the target recognizing antibodies. In some embodiments, the nonspecific antibody is a polyclonal antibody found in normal serum (from an animal not immunized with any of the target proteins). In some embodiments, the nonspecific antibody is a monoclonal antibody to a protein not present in the sample. In some embodiments, the imager moiety directly binds the docking moiety. In some embodiments, the imager moiety indirectly binds the docking moiety through an intermediate moiety.

In some embodiments, a composition comprises: (a) an MTAB; (b) a docking moiety covalently bound to the MTAB; (c) an intermediate moiety having a first domain and a second domain, wherein the first domain is capable of specifically binding to the docking moiety and wherein the second domain is not capable of specifically binding to the docking moiety.

In some embodiments, the MTAB is Protein A, Protein G, Protein A/G, Protein L, or a monovalent antibody fragment. In some embodiments, the docking moiety and the intermediate moiety comprise nucleic acids. In some embodiments, the docking moiety is from about 5 to 20 nucleic acids long, from about 8 to 15, or from about 10 to 12 nucleic acids long. In some embodiments, the intermediate moiety is from about 10 to 40 nucleic acids long, from about 16 to 30, or from about 20 to 24 nucleic acids long.

In some embodiments, a method of making reagents for exchange imaging comprises: (a) providing an MTAB; (b) conjugating the MTAB to a docking moiety to form an MTAB-DM; (c) providing a plurality of intermediate moieties, each having a first domain capable of specifically binding to the docking moiety and a second domain that is not capable of specifically binding to the docking moiety; (d) combining the plurality of intermediate moieties with the MTAB-DM.

In some embodiments, the MTAB is Protein A, Protein G, Protein A/G, Protein L, or a monovalent antibody fragment. In some embodiments, the docking moiety and the intermediate moiety comprise nucleic acids. In some embodiments, the docking moiety is from about 5 to 20 nucleic acids long, from about 8 to 15, or from about 10 to 12 nucleic acids long. In some embodiments, the intermediate moiety is from about 10 to 40 nucleic acids long, from about 16 to 30, or from about 20 to 24 nucleic acids long. In some embodiments, the plurality of intermediate moieties is combined with the MTAB-DM in a batch reaction. In some embodiments, the plurality of intermediate moieties is combined with the MTAB-DM separately.

In some embodiments, a kit for exchange imaging of at least two targets in a sample comprises: (a) at least two different MTAB-DM reagents comprising a MTAB and a docking moiety capable of specifically binding a imager moiety; (b) optionally at least two different target-recognizing antibodies; (c) at least two imager moieties labeled with observable moieties and capable of specifically binding to the MTAB-DM reagents, respectively; (d) optionally at least one antibody that does not specifically bind to any of the targets.

In some embodiments, the MTAB is chosen from Protein A, Protein G, Protein A/G, Protein L, or a monovalent fragment of an antibody. In some embodiments, the docking moiety is a nucleic acid docking moiety and the imager moiety is nucleic acid imager moiety. In some embodiments, the docking moiety is a protein, peptide, or chemical compound and the imager moiety is a complementary protein, peptide, or chemical compound. In some embodiments, the docking moiety and imager moiety are streptavidin and biotin, respectively in either order. In some embodiments, the MTAB and docking moiety are conjugated by using streptavidin or conjugation docking moieties such as SNAP-tag®, CLIP-tag™, HaloTag®, and AviTag™. In some embodiments, the MTAB-DM is capable of binding at least two different target-recognizing antibodies with an affinity of from about 1 fM to 1 nM. In some embodiments, the observable moiety is an optically observable moiety. In some embodiments, the observable moiety is a P-dot, a fluorescent protein, a fluorescent nucleic acid, a Q-dot, a nanoparticle, or a SERS reporter. In some embodiments, a method for exchange imaging employing the reagents described herein.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

In FIG. 3A, the docking moiety directly binds to the imager moiety. In FIG. 3B, the docking moiety binds to an intermediate moiety and the intermediate moiety binds to the imager moiety.

DESCRIPTION OF THE SEQUENCES

Figure 1:
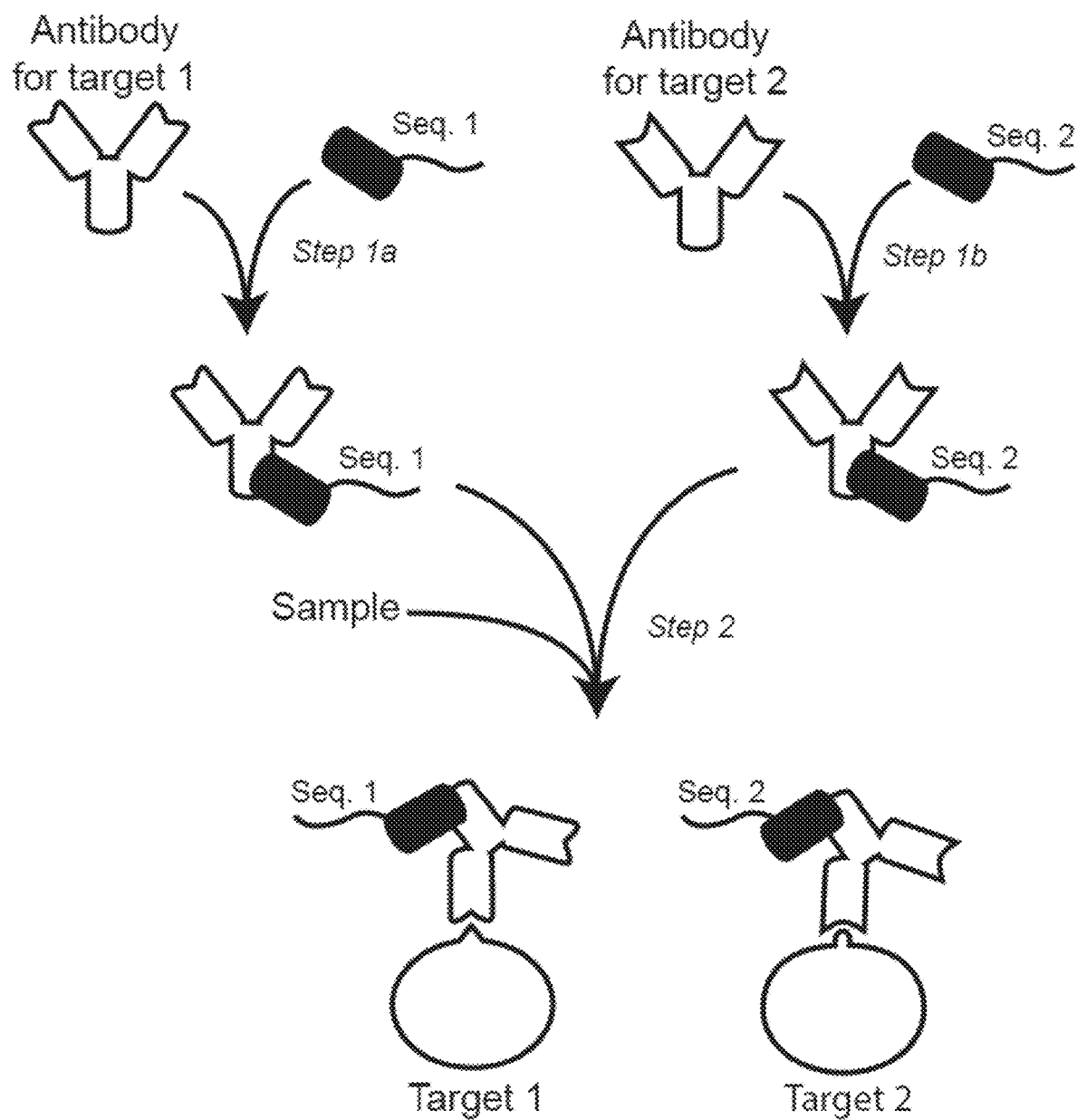
FIG. 1 illustrates an embodiment of MTAB-DMs to label two targets. Antibody to target 1 has a triangular shape on the binding end and antibody to target 2 has a half-circle shape on the binding end. The black rectangle represents the MTAB and the Seq. tail represents the docking moiety.

Table 1 describes certain sequences referenced in this application.

TABLE 1

| Description | Sequence | SEQ ID NO |
|---|---|---|
| Docking moiety1 | 5'-TTGCCACCTTCG-3' | 1 |
| Docking moiety2 | 5'-TAACGGTCAAGC-3' | 2 |
| Docking moiety3 | 5'-CGTAGCCCTGAC-3' | 3 |
| Docking moiety4 | 5'-TGCTGCCTCTTT-3' | 4 |
| Imager moiety1 | 5'-CGAAGGTGGCAA-3' | 5 |
| Imager moiety2 | 5'-GCTTGACCGTTA-3' | 6 |
| Imager moiety3 | 5'-GTCAGGGCTACG-3' | 7 |
| Imager moiety4 | 5'-AAAGAGGCAGCA-3' | 8 |
| Protein A from *Stapylococcus aureus* | MKKKNIYSIR KLGVGIASVT LGTLLISGGV TPAANAAQHD EAQQNAFYQV LNMPNLNADQ PNGFIQSLKD DPSQSANVLG EAQKLNDSQA PKADAQQNKF NKDQQSAFYE ILNMPNLNEE QRNGFIQSLK DDPSQSTNVL GEAKKLNESQ APKADNNENK EQONAFYEIL NMPNLNEEQR NGFIQSLKDD PSQSANLLAE AKKLNESQAP KADNKENKEQ QNAFYEILHL PNLNEEQRNG FIQSLKDDPS QSANLLAEAK KLNDAQAPKA DNKENKEQQN AFYEILHLPN LTEEQRNGFI QSLKDDPSVS KEILAEAKKL NDAQAPKEED NNKPGKEDGN KPGKEDGNKP GKEDNKKPGK EDGNKPGKED NEKPGKEDGN KPGKEDGNKP GKEDGNKPGK EDGNEPGKED GNGVHVVKPG DTVNDIAKAN GTTADKIAAD NKLADKNMIK PGQELVVDKK QPANHADANK AQALPETGEE NPFIGTTVFG GLSLALGAAL LAGRRREL | 9 |
| Protein G from *Streptococcus sp.* group G | MEKEKKVKYF LRKSAFGLAS VSAAFIVGST VFAVDSPIED TPIIRNGGEL TNLLGNSETT LALRNEESAT ADLTAAAVAD TVAAAAAENA GAAAWEAAAA ADALAKAKAD ALKEFNKYGV SDYYKNLINN AKTVEGVKDL QAQVVESAKE ARISEATDGL SDFIKSQTPA EDTVKSIELA EAKVLANREL DKYGVSDYHK NLINNAKTVE GVKDLQAQVV ESAKKARISE ATDGLSDFLK SQTPAEDTVK SIELAEAKVL ANRELDKYGV SDYYKNLINN AKTVEGVKAI IDEILAAIPK TDTYKLILNG KTLKGETTTE AVDAATAEKV FKQYANDNGV DGEWTYDDAT KTFTVTEKPE VIDASELTPA VTTYKLVING KTLKGETTTE AMTAATAEKV FKQYANDNGV DGEWTYDDAT KTFTVTEKPE VIDASELTPA VTTYKLVING KTLKGETTTK AVDAETAEKA FKQYANDNGV DGVWTYDDAT KTFTVTEMVT EVPGDAPTEP EKPEASIPLV PLTPATPIAK DDAKEDDTKK EDAKKPEAKE EDAKKAETLP TTGEGSNPFF LAAALAVMAG AGALAVASKR KED | 10 |
| Protein L from *Peptostreptococcus magnus* | MKINKKLLMA ALAGAIVVGG GANAYAAEED NTDNNLSMDE ISDAYFDYEG DVSDSVDPVE EEIDEALAKA LAEAKETAKK HIDSLNHLSE TAKKIAKNDI DSATTINAIN DIVARADVMF RKTAEKEEAE KLAAAKETAK KHIDELKHLA DKTKELAKRD IDSATTINAI NDIVARADVM ERKTAEKEEA EKLAAAKETA KKHIDELKHL ADKTKELAKR DIDSATTIDA INDIVARADV MERKLSEKET PEPEEEVTIK ANLIFADGST QNAEFKGTFA KAVSDAYAYA DALKKDNGEY TVDVADKGLT LNIKFAGKKE KPEEPKEEVT IKVNLIFADG KTQTAEFKGT FEEATAKAYA YADLLAKENG EYTADLEDGG NTINIKFAGK ETPETPEEPK EEVTIKVNLI FADGKIQTAE FKGTFEEATA KAYAYANLLA KENGEYTADL EDGGNTINIK EAGKETPETP EEPKEEVTIK VNLIFADGKT QTAEFKGTFE EATAEAYRYA DLLAKVNGEY TADLEDGGYT INIKFAGKEO PGENPGITID EWLLKNAKEE AIKELKEAGI TSDLYFSLIN KAKTVEGVEA LKNEILKAHA GEETPELKDG YATYEEAEAA AKEAIKNDDV NNAYEIVQGA DGRYYYVLKI EVADEEEPGE DTPEVQEGYA TYEEAKAAAK EALKEDKVNN AYEVVQGADG RYYYVIKIED KEDEQPGEEP GENPGITIDE WLLKNAKEDA IKELKEAGIS SDIYFDAINK | 11 |

TABLE 1-continued

Sequences

| Description | Sequence | SEQ ID NO |
|---|---|---|
| | AKTVEGVEAL KNEILKAHAE KPGENPGITI DEWLLKNAKE AAIKELKEAG ITAEYLFNLI NKAKTVEGVE SLKNEILKAH AEKPGENPGI TIDEWLLKNA KEDAIKELKE AGITSDIYFD AINKAKTIEG VEALKNEILK AHEKDEEPGK KPGEDKEPED KKPGEDKKPE DKKPGEDKKP EDKKPGKTDK DSPNKKKKAK LPKAGSEAEI LTLPAAAIST AAGAYVSLKK PK | |
| 5' ATTO488-labeled oligonucleotide | 5'-TCTGCTTTCCCGTTATACATCTA-3' | 12 |
| Docking moiety | TCTGCTTTCCCG | 13 |

DESCRIPTION OF THE EMBODIMENTS

I. Multiplexed Imaging Using Improved Methods to Attach Docking Moieties to Target-Recognizing Antibodies Multiplexed imaging using improved methods to attach docking moieties to target-recognizing antibodies is described herein. Once the docking moieties have been attached to target-recognizing antibodies, the antibodies labeled with the docking moieties can be used in a variety of super-resolution or standard resolution imaging.

For example, in some contexts, the multiplexed imaging may be super-resolution imaging. One class of super-resolution imaging techniques is called stochastic super-resolution, which is characterized by images containing blinking or flickering signals from fluorescent labels. Depending on the method to process the data, stochastic super-resolution can be divided into single-molecule localization microscopy (SMLM) and super-resolution optical fluctuation imaging (SOFI). The blinking or flickering behavior can be achieved by several mechanisms such as photo-activation of organic dyes (e.g., in a technique widely known as stochastic optical reconstruction microscopy, or STORM), photo-switching of fluorescent proteins (e.g., in a technique widely known as photo activated localization microscopy, or PALM), and inherent blinking properties of quantum dots.

PAINT (point accumulation for imaging in nanoscale topography) is one simple and powerful technique to achieve blinking or flickering signals from fluorescent labels, which is caused by dynamic and transient noncovalent interactions between a non-observable docking moiety attached to a target-recognizing molecule and an observable molecule in solution. PAINT-based super-resolution imaging has been adopted to immunofluorescence by Jungmann et al., Nat methods 11(3):313-8 (2014) (Ref: PMID 24487583), where an antibody is used as the target-recognizing molecule. Here we call this technique PAINT-based Super-Resolution Immunofluorescence (PSRIF).

In any of these imaging methods, instead of (a) attaching docking moieties directly to target-recognizing antibodies or (b) limiting the number and type of target-recognizing antibodies so that there is a 1:1 correspondence between target-recognizing antibodies and secondary antibodies that can label them (one mouse target-recognizing antibody and one rabbit anti-mouse secondary antibody; one rat target-recognizing antibody and one rabbit anti-rat secondary antibody, etc.), docking moieties may be indirectly attached to target-recognizing antibodies using monovalent tight antibody binders (MTABs). MTABs and their affinities for target-recognizing antibodies are described in Section I.A below. As shown in FIG. 1 (steps 1a and 1b), different target-recognizing antibodies may be complexed with their corresponding MTAB-DMs in parallel thus introducing different docking moieties to different target-recognizing antibodies.

A. Monovalent Tight Antibody Binders

In some embodiments, monovalent tight antibody binders (MTABs) may be used to attach docking moieties to target-recognizing antibodies. MTABs include Protein A, Protein G, and monovalent monoclonal and polyclonal antibodies against constant regions of other antibodies (e.g., Fab, Fab', Fv, and scFv). Protein A and Protein G are bacterial-derived proteins that are known to bind immunoglobulins. Each of these types of MTABs are described further below.

The affinity of the MTABs to the target-recognizing antibodies, measured by dissociation constant ($K_d$), may be in the range of from about 1 fM to 1 nM, from about 1 fM to 1 pM, or from about 1 pM to 1 nM. In some embodiments, the $K_d$ values may be less than or equal to about 1 fM, 10 fM, 100 fM, 1 pM, 10 pM, 100 pM, or 1 nM. The affinity for a candidate MTAB for the target-recognizing antibodies for use in any particular imaging experiment may be assessed by ELISA, surface plasmon resonance, isothermal calorimetry titration, and fluorescence-based assays to measure binding rate and/or dissociation rate. Other options for assessing whether an MTAB may be paired with a target-recognizing antibody are discussed below in Section I.C.

Depending on the target-recognizing antibody type, different MTABs may be selected. Table 2 provides guidance in this regard. The following table provides information on the affinities of Protein A and Protein G for various immunoglobulin types.

TABLE 2

Affinity of Protein A and Protein G to Immunoglobulin Types and Species

| Species | Immunoglobulin | Binding to Protein A | Binding to Protein G |
|---|---|---|---|
| Human | IgG (normal) | ++++ | ++++ |
| | IgG1 | ++++ | ++++ |
| | IgG2 | ++++ | ++++ |

TABLE 2-continued

Affinity of Protein A and Protein G to Immunoglobulin Types and Species

| Species | Immunoglobulin | Binding to Protein A | Binding to Protein G |
|---|---|---|---|
| | IgG3 | − | ++++ |
| | IgG4 | ++++ | ++++ |
| | IgM | − | − |
| | IgA | − | − |
| | IgE | − | − |
| Mouse | IgG1 | + | ++++ |
| | IgG2a | ++++ | ++++ |
| | IgG2b | +++ | +++ |
| | IgG3 | ++ | +++ |
| Rat | IgG1 | − | + |
| | IgG2a | − | ++++ |
| | IgG2b | − | ++ |
| | IgG2c | + | ++ |
| Goat | IgG | +/− | ++ |
| Rabbit | IgG | ++++ | +++ |
| Sheep | IgG | +/− | ++ |

In this application, MTAB is monovalent; meaning that one molecule of MTAB binds only one molecule of the target-recognizing antibody. Therefore, a full-length secondary antibody cannot be a MTAB. This is because one molecule of full-length secondary antibody can bind two target-recognizing, primary antibodies at the same time, and one molecule of primary antibody can be bound by multiple molecules of the secondary antibody (regardless of whether the secondary antibody is monoclonal, oligoclonal, or polyclonal) at the same time; such multivalent interaction could create a high molecular-weight complex that may not penetrate the sample as well.

1. Protein A

Protein A is composed of five homologous Ig-binding domains that fold into a three-helix bundle. Each domain is able to bind proteins from many mammalian species, most notably IgGs. It binds the heavy chain within the Fc region of most immunoglobulins and also within the Fab region of some antibodies. One well-characterized version of Protein A is from *Staphylococcus aureus*, although other sources of Protein A may also be used. Protein A can be isolated from *Staphylococcus aureus* or it may be produced recombinantly. Pierce™ Recombinant Protein A can be used from Thermo Fisher Scientific. Fragments, variants, and derivatives of Protein A may also be used as long as they bind to the target-recognizing antibodies sufficiently and are included in any reference to the term Protein A unless the term full-length Protein A is used.

Protein A is a well-characterized protein and its ability (whether in full length form or fragments thereof) to bind to immunoglobulin Fc domains is understood in the art. See Graille, et al., Crystal Structure of a *Staphylococcus aureus* Protein A domain complexed with the Fab fragment of a human IgM antibody: Structural basis for recognition of B-cell receptors and super antigen activity, PNAS 97(10): 5399-5404 (2000). In some instances, the Protein A includes helices II and III of domain D. Thus, an appropriate Protein A can be selected once the target-recognizing antibodies are selected.

The sequence of Protein A is provided as SEQ ID NO: 9. The term Protein A includes any polypeptide that is at least about 90%, 91%, 92%, 93%, 94%, 95%, 96%, 97%, 98%, 99%, or 100% identical to SEQ ID NO: 9 over the length of the polypeptide (meaning that shorter sequences are included if they meet the percentage homology over the length of the shorter sequence). In some embodiments, fragments of Protein A may be at least about 50, 100, 150, 200, 250, 300, 350, 400, 450, or 500 amino acids long.

Derivatives of Protein A, such as chemically-modified Protein A may also be included herein.

2. Protein G

Like Protein A, Protein G is a protein produced by bacteria that binds to immunoglobulin. Protein G is produced by group C and G Streptococcal bacteria and binds to the Fab and Fc regions of antibodies. It also binds to albumin and cell-surfaces and thus, is available in a recombinant form that lacks the albumin and cell surface binding sites. Fragments, variants, and derivatives of Protein G may also be used as long as they bind to the target-recognizing antibodies sufficiently and are included in any reference to the term Protein G unless the term full-length Protein G is used. In some embodiments, recombinant Protein G lacking the albumin binding site may be employed. Pierce™ Recombinant Protein G can be used from Thermo Fisher Scientific and lacks both the albumin and cell-surface binding domains.

Protein G is a well-characterized protein and its ability (whether in full length form or fragments thereof) to bind to immunoglobulin Fc domains is understood in the art. See Sjöbring et al., Streptococcal Protein G, JBC 266(1):399-405 (1991). In some embodiments, Protein G includes the C1 domain of Protein G. Thus an appropriate Protein G can be selected once the target-recognizing antibodies are selected.

The sequence of Protein G is provided as SEQ ID NO: 10. The term Protein G includes any polypeptide that is at least about 90%, 91%, 92%, 93%, 94%, 95%, 96%, 97%, 98%, 99%, or 100% identical to SEQ ID NO: 10 over the length of the polypeptide (meaning that shorter sequences are included if they meet the percentage homology over the length of the shorter sequence). In some embodiments, fragments of Protein G may be at least about 50, 100, 150, 200, 250, 300, 350, 400, 450, or 500 amino acids long.

Derivatives of Protein G, including chemically modified Protein G may also be included herein.

3. Protein A/G

Protein A/G is a recombinant fusion protein that combines IgG binding domains of both Protein A and Protein G. Full length Protein A/G contains four Fc binding domains from Protein A and two from Protein G. Protein A/G binds to all subclasses of human IgG, making it useful for binding to antibodies whose subclasses have not been determined.

Fragments, variants, and derivatives of Protein A/G may also be used as long as they bind to the target-recognizing antibodies sufficiently and are included in any reference to the term Protein A/G unless the term full-length Protein A/G is used. Pierce™ Recombinant Protein A/G can be used from Thermo Fisher Scientific. Derivatives of protein A/G, including chemically modified protein A/G may also be included herein.

4. Protein L

Protein L is another protein produced by bacteria that binds to immunoglobulin. Protein L is produced by *Peptostreptococcus magnus* and binds to immunoglobulins through L chain interaction, from which the name was suggested. Fragments, variants, and derivatives of Protein L may be used as long as they bind to the target-recognizing antibodies sufficiently and are included in any reference to the term Protein L unless the term full-length Protein L is used. Pierce™ Recombinant Protein L can be used from Thermo Fisher Scientific. Protein L binds to antibodies containing kappa light chains.

Protein L is a well-characterized protein and its ability (whether in full length form or fragments thereof) to bind to immunoglobulin Fc domains is understood in the art. See Kastern et al., Structure of Peptostreptococcal Protein L and Identification of a Repeated Immunoglobulin Light Chain-binding Domain, JBC 267(18):12820-12825 (1992). In some embodiments, Protein L includes at least one, two, three, four, or five B repeats. Thus, an appropriate Protein L can be selected once the target-recognizing antibodies are selected.

The sequence of Protein L is provided as SEQ ID NO: 11. The term Protein L includes any polypeptide that is at least about 90%, 91%, 92%, 93%, 94%, 95%, 96%, 97%, 98%, 99%, or 100% identical to SEQ ID NO: 11 over the length of the polypeptide (meaning that shorter sequences are included if they meet the percentage homology over the length of the shorter sequence). In some embodiments, fragments of Protein L may be at least about 50, 100, 150, 200, 250, 300, 350, 400, 450, 500, 550, 600, 650, 700, 750, 800, 900, or 950 amino acids long.

Derivatives of Protein L, including chemically modified Protein L may also be included herein.

5. Monovalent Fragments or Derivatives of Antibodies

Monovalent antibodies may also be used as long as they will bind sufficiently to the target-recognizing antibodies in question. This term includes any monovalent antibody format including any fragments that comprise the variable region of an antibody. These include, but are not limited to, Fab, Fab', Fv, and scFv fragments of antibodies. Monovalent fragments of secondary antibodies against the target-recognizing antibodies may be used an MTABs. For example, if the target-recognizing antibodies are murine antibodies, a monovalent fragment or derivative of a rabbit-anti-mouse antibody may be employed as a MTAB. Such antibody fragment MTABs may be fragmented enzymatically from whole antibodies or they may be prepared recombinantly.

B. Docking Moieties

Docking moieties (or DMs), as discussed above, may be bound to MTABs to allow for easy complexing with target-recognizing antibodies.

In some embodiments, the docking moiety comprises nucleic acids. When the docking moiety is a nucleic acid, it may also be described as a docking strand. In some embodiments, the nucleic acids are single stranded nucleic acids such as single stranded DNA, RNA, or a nucleic acid analog. A nucleic acid analog may include an altered phosphate backbone, an altered pentose sugar, and/or altered nucleobases. Nucleic acid analogs may include, but are not limited to, 2'-O-methyl ribonucleic acid, 2'-fluoro ribonucleic acid, peptide nucleic acid, morpholino and locked nucleic acid, glycol nucleic acid, and threose nucleic acid.

In some embodiments, the docking moiety comprises single-stranded nucleic acids and may be from about 5 to 20 nucleic acids long, from about 8 to 15, or from about 10 to 12 nucleic acids long. In some embodiments, the docking moiety is about 5, 8, 9, 10, 11, 12, 13, 14, 15, 18, or 20 nucleic acids long.

In some embodiments, the docking moiety is a protein, a peptide, or a chemical compound. Many proteins and domains of proteins that can serve as docking moieties are known to interact with other proteins, domains or peptides that can serve as imager moiety moieties, as described in Section I.F.1 below. Some of the best known domains include SH2, SH3, and WD40 domains. In many cases the binding partner of these proteins and domains are known and can be engineered to have the desired affinity. In some cases, a native binding pair from one organism (e.g. yeast) can be used to study samples from another organism (e.g., human) to avoid cross interaction. Many chemical compounds can make specific interactions with other compounds or proteins, where the affinity is either directly suitable for this context or can be engineered to be suitable. For example, biotin and avidin/streptavidin interact with sufficient specificity. Many other chemical compounds, such as digoxigenin, fluorescein, tacrolimus and rapamycin also have well known binding partners.

1. Indirect Conjugation

Figure 3A:
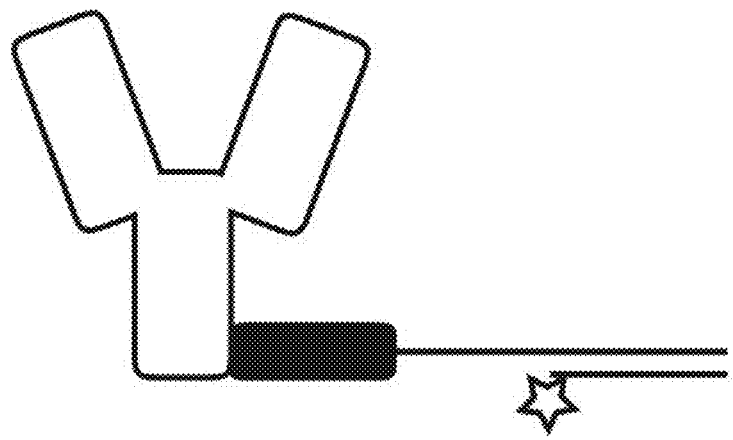
FIGS. 3A-3B show direct and indirect binding of the docking moiety to the imager moiety.
Figure 3B:
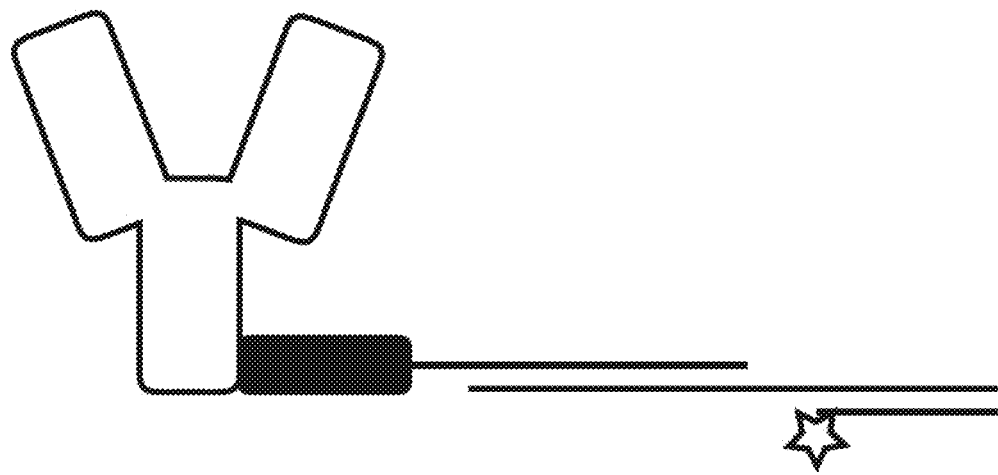

In some embodiments, such as the embodiment shown in FIG. 3B, the docking moiety may bind to the imager moiety indirectly, such as through an intermediate moiety. For instance, when the docking moiety and the imager moiety are nucleic acids, an intermediate moiety comprising nucleic acids may be used as long as the intermediate moiety has a first region complementary to the docking moiety and a second region complementary to the imager moiety. In this embodiment, it is not necessary for the docking moiety to be complementary to the imager moiety. Using a universal docking moiety can provide advantages in that only one type of MTAB-DM is required to be prepared and easy to synthesize and very inexpensive oligonucleotides can be used as intermediate moieties when the docking moiety is a nucleic acid docking moiety.

Thus in some embodiments, a composition comprises an MTAB, a docking moiety bound to the MTAB (optionally bound covalently), and an intermediate moiety having a first domain and second domain, wherein the first domain is capable of specifically binding the docking moiety and wherein the second domain is not capable of specifically binding to the docking moiety.

Additionally, in some embodiments, a method of making reagents for exchange imaging comprises providing an MTAB; conjugating the MTAB to a docking moiety to form an MTAB-DM (optionally with a covalent bond), providing plurality of intermediate moieties, each having a first domain capable of specifically binding to the docking moiety and a second domain that is not capable of specifically binding to the docking moiety; combining the plurality of intermediate moieties with the MTAB-DM. In some embodiments, the plurality of intermediate moieties is combined with the MTAB-DM in a batch reaction. This results in a mixed population of MTAB-DM:intermediate moieties. In some embodiments, the plurality of intermediate moieties is combined with the MTAB-DM in separate parallel combinations. This results in different substantially homogeneous populations of MTAB-DM:intermediate moieties.

In some embodiments, an intermediate moiety is from about 10 to 40 nucleic acids long, from about 16 to 30, or from about 20 to 24 nucleic acids long

C. Determine the Whether an MTAB-DM Can Be Used with a Predetermined Antibody Many candidates for MTAB (e.g., Protein A, Protein G, Protein L, Protein A/G, and polyclonal Fabs) are commercially available from vendors such as Abcam, Jackson ImmunoResearch, Santa Cruz Biotechnology, and Thermo Fisher. In addition, some candidates for MTAB can be produced from commercially available precursors. For example, polyclonal Fab' can be produced by reducing polyclonal F(ab')2 (which is in turn commercially available) with reducing agents such as DTT (Crivianu-Gaita et al., High efficiency reduction capability for the formation of Fab' antibody fragments from F(ab)2 units, Biochemistry and Biophysics Reports 2:23-28 (2015)). These MTAB candidates can be used to conjugate with the docking moiety (see Section I.D) to form MTAB-DM candidates.

Although there are many choices of MTAB-DM, owing to the fact that multiple types of proteins can serve as MTAB, it is important to ensure that for a given antibody, the MTAB-DM of choice is suitable, which means that two criteria may be met. First, in some embodiments, the binding of MTAB-DM does not cause the antibody to lose its ability to bind its target tightly. Second, in some embodiments, the MTAB-DM binds the antibody with sufficient affinity that the antibody:MTAB-DM complex does not dissociate to a significant level during the experiment.

As for the second criteria, a lower level of dissociation can provide advantages; however, a tolerable level of dissociation depends on the application. If the application is qualitative, the target is abundant, or the detection method is sensitive enough, even a small fraction of remaining antibody:MTAB-DM complex can be detected. Thus, the tolerable level of dissociation may be more than 80%. In contrast, in more quantitative applications, when the target abundance is low, or when the detection method is not sensitive, the tolerable level of dissociation may be less than 5%. In some embodiments, less than or equal to about 1%, 2%, 3%, 4%, 5%, 10%, 15%, 20%, 30%, 40%, 50%, 60%, 70%, or 80% of the MTAB-DM dissociates from the target-recognizing antibody during the imaging.

It is common knowledge that some protein that may serve as MTAB for some antibodies may not serve as MTAB for other antibodies. For example, Protein A is known to bind rabbit IgG tightly but bind mouse IgG1 poorly. In addition to relying on known binding criteria, if suitability of a protein to serve as MTAB is unknown, it can be easily experimentally tested.

Given a pre-specified antibody and a pre-specified application, whether a MTAB-DM can bind the antibody tightly enough can be experimentally evaluated in a straightforward manner Suppose (1) the property of the primary antibody dictates that the primary antibody staining takes X hours at temperature Temp-X, (2) the application dictates that after the antibody:MTAB-DM complexes are washed, there is additional Y hour of other steps at temperature Temp-Y before the target is imaged, (3) the application dictates that the maximum tolerable level of dissociation is Z %, and (4) the affinity between the docking moiety and the Imager moiety has been pre-determined to be sufficiently high (e.g., negligible dissociation is expected after X hours at temperature Temp-X and Y hours at temperature Temp-Y, using any one of the many methods known to the skilled artisan), one can use the protocol in Examples 3 and/or 4 below to test whether the MTAB-DM binds the antibody stable enough.

D. Methods for Conjugating Docking Moieties to MTABs

MTABs may be conjugate to docking moieties to form MTAB-DM conjugates.

Most proteins, including those that can function as MTABs, have lysine residues (which contain a primary amine group on its side chain) on their surface. In this case one can use an amine-reactive cross-linker to conjugate the docking moiety to MTAB. In some embodiments, linkage may be achieved using bi-functional cross-linkers. For sample, succinimidyl 4-(N-maleimidomethyl)cyclohexane-1-carboxylate (SMCC), SM(PEG)2 (Thermo Fisher Cat #22102) and the like can be used to link lysine residues on the MTAB with the thiol-group on a thiol-containing docking moiety (e.g., if the docking moiety is a peptide and contains cysteine) or thiol-modified docking moiety (e.g., thiol-modified oligonucleotide). Alternatively, one may use azido-NHS ester (Thermo Fisher Cat #88902) to introduce an azide group to the lysine residue of the MTAB, modify the docking moiety with an alkyne group, and use copper-assisted Click Chemistry to link the azide and the alkyne groups.

Many proteins also have surface thiol groups, as part of the cysteine residue, that can be used as conjugation handle. One can use SMCC, SM(PEG)2 or the like to link the thiol group of the MTAB and the amine group on an amine-containing docking moiety (e.g., if the docking moiety is a peptide and contains lysine or N-terminal amine) or amine-modified docking moiety (e.g., amine-modified oligonucleotide) Similarly, one may use Azido-PEG3-Maleimide (Santa Cruz Biotechnology Cat #sc-496404), Azide-PEG4-maleimide (Click Chemistry Tools Cat #AZ10725) and the like to introduce an azide group to the cysteine residue of the MTAB, modify the docking moiety with an alkyne group, and use copper-assisted Click Chemistry to link the azide and the alkyne groups.

If the MTAB is produced recombinantly, one can fuse another conjugation-friendly conjugation tag protein, such as streptavidin (or its derivative or related protein), or commercially-available conjugation docking moieties such as SNAP-tag®, CLIP-tag™, HaloTag®, and AviTag™, in order to facilitate conjugation to an oligonucleotide docking moiety.

E. Target-Recognizing Antibody

The target-recognizing antibody refers to both full-length antibodies and antigen binding fragments thereof, including antibody-like molecules that can be used to detect the target molecule and any engineered variation or fragment of an antibody that contains a domain for binding of the MTAB. For example, single chain antibodies, scFv-Fcs, and the like may be employed as target-recognizing antibodies. Antibody refers to any immunoglobulin from any species that can specifically recognize a target molecule. Therefore, unless the term full-length antibody is used, the term antibody includes antigen-binding fragments of antibodies that contain a domain for binding of the MTAB.

Once the targets in the sample are identified, a person of ordinary skill in the art can either generate an antibody for that target or find one that is commercially available. Either serum-purified or recombinant antibodies may be used. Various commercial vendors provide a wide array of primary antibodies that can serve in these embodiments as target-recognizing antibodies including those available against a wide plurality of targets from vendors including Abcam, Sigma-Aldrich, and Pierce Antibodies of Thermo Fisher Scientific.

In some embodiments, all of the target-recognizing antibodies are applied to the sample and allowed to stain the sample simultaneously. This allows for maximum efficiency and the shortest experimental duration as antibody incubation can be lengthy depending on the concentration of each target-recognizing antibody employed. In other embodiments, such as if two or more antibodies interfere with at least one of their binding to their intended targets, they can be divided into separate batches for incubation and binding to their sample and the imaging can comprise at least two sets of reactions with at least one set occurring in a multiplexed format with more than one target-recognizing antibody applied to the sample at the same time. The application of multiple target-recognizing antibodies simultaneously to a sample is shown in FIG. 1.

F. Imager Moieties and Observable Moieties

Imager moieties bound to observable moieties allow for imaging of the docking moieties. Imager moieties may bind to the docking moieties either transiently or nontransiently. Transient binding refers to a binding interaction where at least one of the following is true (1) the dissociation rate constant of the bound complex (often expressed as $k_{off}$) is 0.1 $s^{-1}$ or higher or (2) the dissociation constant (often expressed $K_d$) is 100 nM or higher. Non-transient binding refers to a binding interaction where dissociation rate constant of the bound complex ($k_{off}$) is lower than 0.1 $s^{-1}$, AND the dissociation constant ($K_d$) is lower than 100 nM. Options for transient and non-transient binding are discussed further in U.S. Provisional Appln. No. 62/327,604.

1. Imager Moieties

Imager moieties are capable of specifically binding to docking moieties as described above in Section I.B. When a docking moiety is a nucleic acid, the imager moiety also comprises nucleic acids. If an imager moiety is comprised of nucleic acids, it may also be described as an imager strand. In some embodiments, the nucleic acids are single stranded nucleic acids such as single stranded DNA, RNA, or a nucleic acid analog. A nucleic acid analog may include an altered phosphate backbone, an altered pentose sugar, and/or altered nucleobases. Nucleic acid analogs may include, but are not limited to, 2'-O-Methyl ribonucleic acid, 2'-fluoro ribonucleic acid, peptide nucleic acid, morpholino and locked nucleic acid, glycol nucleic acid, and threose nucleic acid.

By specifically binding, if the docking moieties and the imager moieties are nucleic acids they may hybridize under high ionic strength buffer conditions; for example, high ionic strength buffer conditions (e.g. 1× saline sodium citrate buffer, or 150 mM, 200 mM, 300 mM, 400 mM, 500 mM, or 600 mM sodium chloride in phosphate buffer) may be employed at room temperature to evaluate hybridization.

In some embodiments, the imager moiety comprises single-stranded nucleic acids and may be from about 5 to 20 nucleic acids long, from about 8 to 15, or from about 10 to 12 nucleic acids long. In some embodiments, the imager moiety is about 5, 8, 9, 10, 11, 12, 13, 14, 15, 18, or 20 nucleic acids long.

In some embodiments, imager moiety is a protein, peptide, or a chemical compound, as a partner to the docking moiety options discussed above in Section I.B above.

In some embodiments, the docking moiety may bind to the imager moiety indirectly, such as through an intermediate moiety. For instance, when the docking moiety and the imager moiety are nucleic acids, an intermediate moiety comprising nucleic acids may be used as long as the intermediate moiety has a first region complementary to the docking moiety and a second region complementary to the imager moiety. In this embodiment, it is not necessary for the docking moiety to be complementary to the imager moiety.

For example, Table 3 shows the following docking moiety and imager moiety pairs can be used to label different target-recognizing antibodies, where docking moiety 1 pairs with imager moiety1 and so on. Other similar pairs can easily be prepared.

TABLE 3

Docking Moiety and Imager Moiety Pairs

| Description | Sequence | SEQ ID NO |
| --- | --- | --- |
| Docking moiety1 | 5'-TTGCCACCTTCG-3' | 1 |
| Docking moiety2 | 5'-TAACGGTCAAGC-3' | 2 |
| Docking moiety3 | 5'-CGTAGCCCTGAC-3' | 3 |
| Docking moiety4 | 5'-TGCTGCCTCTTT-3' | 4 |
| Imager moiety1 | 5'-CGAAGGTGGCAA-3' | 5 |
| Imager moiety2 | 5'-GCTTGACCGTTA-3' | 6 |
| Imager moiety3 | 5'-GTCAGGGCTACG-3' | 7 |
| Imager moiety4 | 5'-AAAGAGGCAGCA-3' | 8 |

2. Observable Moieties

Various observable moieties may be affixed to the imager moieties described herein. In some embodiments, any observable moiety may be employed and in some embodiments the moiety is optically observable. The moiety may be signal absorbing or signal emitting. Of signal emitting molecules, molecules that fluoresce may be used, such as organic small molecules, including, but not limited to fluorophores, such as, but not limited to, fluorescein, rhodamine, cyanine dyes, Alexa dyes, DyLight® dyes, Atto dyes, etc.

In some embodiments organic polymers, such as P-dots may be employed. In some embodiments, the observable moiety may be a biological molecule, including but not limited to a fluorescent protein or fluorescent nucleic acid (including fluorescent RNAs including Spinach and its derivatives). In some embodiments, the observable moiety may be an inorganic moiety including Q-dots. In some embodiments, the observable moiety may be a moiety that operates through scattering, either elastic or inelastic scattering, such as nanoparticles and Surface Enhanced Raman Spectroscopy (SERS) reporters (e.g., 4-Mercaptobenzoic acid, 2,7-mercapto-4-methylcoumarin). In some embodiments, the observable moiety may be chemiluminescence/ electrochemiluminescence emitters such as ruthenium complexes and luciferases. The observable moiety may generate an optical signal, an electromagnetic signal (across the entire electromagnetic spectrum), atomic/molecular mass (e.g. detectable by mass spectrometry), tangible mass (e.g., detectable by atomic force microscope), current or voltage.

In some embodiments, a single type of observable moiety can be bound to all of the different imager moieties. In such an instance, imager moiety 1 with the observable moiety can be applied and imaged, a washing step performed, and imager moiety 2 with the observable moiety can be applied and imaged, and so on. Computerized assembly can produce a final image.

Alternatively, different observable moieties can be bound to at least some (or even all) of the different imager moieties for use in an imaging protocol. This allows for either batched imaging steps (if some but not all imager moieties have different observable moieties) or a single imaging step (if all imager moieties have different observable moieties). One of skill in the art can select an appropriate observable moiety or series of observable moieties to fit the experimental conditions, the number of targets for imaging, the materials they have at hand, etc.

G. Method Steps

The imaging described herein follows the basic outline of exchange imaging with extra steps and components as described herein. (1) As a first step, MTAB-DM conjugates are prepared, (2) the MTAB-DMs combined with target-recognizing antibody to form MTAB-DM:target-recognizing antibody complexes; (3) the MTAB-DM:target-recognizing antibody complexes incubated with the sample followed by an optional washing step, (4) imager moieties with observable moieties applied, each specifically recognizing a docking moiety to label either all or a subset of docking moieties, and imaging the corresponding targets, (5) optionally removing the set of imager moieties used in step (4) or inactivating the observable moieties on such imager moieties followed by an optional washing step, and (6) optionally using another set of imager moieties, each specifically recognizing a docking moiety and carrying an observable moiety, to label another subset of docking moieties, and imaging the corresponding subset of targets.

If each imager moiety is labeled with a distinct observable moiety, steps (5) and (6) are not necessary. Depending on the number of observable moieties available to an investigator and the number of targets to be imaged, steps (5) and (6) may also be repeated. In some instances, all of the MTAB-DM:target-recognizing antibody complexes are incubated together in step (3) and in other instances steps (3)-(4) or (3)-(6) are repeated at least once with multiple MTAB-DM:target-recognizing antibody complexes incubated together in at least one of the instances of step (3).

The reaction conditions for incubating the target-recognizing antibody and the sample are well known in the art and take into account the concentration of the target-recognizing antibody available to the investigator, the amount of target present in the sample, the affinity of the target-recognizing antibody for the target, and the time the investigator has available for incubation. After staining, a standard washing step is often performed.

H. Additional Embodiments

1. Adjusting the Amount of MTAB-DM in Relationship to the Amount of Target-Recognizing Antibody Additional optional embodiments may also be employed by adjusting the amount of MTAB-DM in relationship to the amount of target-recognizing antibody.

In some embodiments, the ratio of the target-recognizing antibody and MTAB-DM can be tuned so that no free antibody or MTAB-DM is left before applying the MTAB-DM and target-recognizing antibody to the sample for imaging. If excess free antibody is present in the incubation step prior to imaging, some free antibody may bind to the target without generating a signal. If this occurred, free antibody could lower the overall signaling capacity of the imaging.

Additionally, the potential for reduced accuracy signals can be generated when MTAB-DM intended to bind to a first target-recognizing antibody is present at excess concentrations and binds to second target-recognizing antibody (i.e., recognizing a different target). Thus, depending on the concentration, number of binding sites, and affinity of the MTAB-DM for the target-recognizing antibody, it is possible that some MTAB-DM 1 intended to label target-recognizing antibody 1 would be present in excess from the conjugation to target-recognizing antibody 1 or could dissociate and become available to bind to target-recognizing antibody 2. If MTAB-DM 1 became bound to target-recognizing antibody 2, a reduced accuracy signal could be generated.

By excess, the user should keep in mind that an MTAB-DM preparation may have more than one binding site on each target-recognizing antibody. For example, if a monovalent polyclonal antibody serves as the MTAB, different component antibodies may bind at different locations on a target-recognizing antibody.

Thus, in some embodiments, a purification step may be included to remove the free target-recognizing antibody and/or free MTAB-DM. For example, if the MTAB-DM is smaller in molecular weight than the antibody, one can use ultrafiltration or gel-filtration to separate the antibody:MTAB-DM complex and the free MTAB-DM. For example, this may be used when the MTAB is Fab domain (~50 kD, compared to the target-recognizing antibody which is ~150 kD) and the non-Fab portion of the MTAB-DM is less than 50 kD cumulatively. This may, optionally, be combined with using an initial excess of MTAB-DM so as to prevent an excess of target-recognizing antibody.

2. Employing Nonspecific Antibody

As an optional embodiment, nonspecific antibody may be added to the method described herein. Even if the ideal amount of MTAB-DM is present for the concentration of the target-recognizing antibody, because the antibody:MTAB-DM interaction is noncovalent, it is possible that during the staining, washing, and imaging, a MTAB-DM molecule may dissociate from the antibody it is originally complexed with, and subsequently bind to a second type of target-recognizing antibody bound to second target, creating a reduced accuracy signal.

In some embodiments, as an optional substitute for the optional purification process, one may add nonspecific molecules that can also bind MTAB-DM in a way that competes with the target-recognizing antibody, wherein the nonspecific antibodies will not specifically bind to a component of the sample being imaged. Such nonspecific antibody may be added to the staining, washing, and/or imaging buffer so that if a MTAB-DM molecule dissociates from the antibody it is originally complexed with, it will bind to a target-nonspecific molecule in the solution, rather than binding to an antibody bound to a different target.

One example of such a nonspecific molecule is an antibody or a mixture of such antibodies, which can be found in normal serum (i.e., not immunized with any of the target proteins) from the host species of the target-recognizing antibodies, or immunoglobulin-containing protein mixtures purified from such serum. Alternatively, a monoclonal antibody to a protein unrelated to the sample may be employed as a nonspecific antibody. The nonspecific antibody serves as a sink for any unbound MTAB-DM, which was either present in excess after association with the target-recognizing antibody or which may happen to dissociate from the target-recognizing antibody during the imaging process.

3. 2-Step Staining and Sequential Staining Using MTAB-DMs

Figure 2:
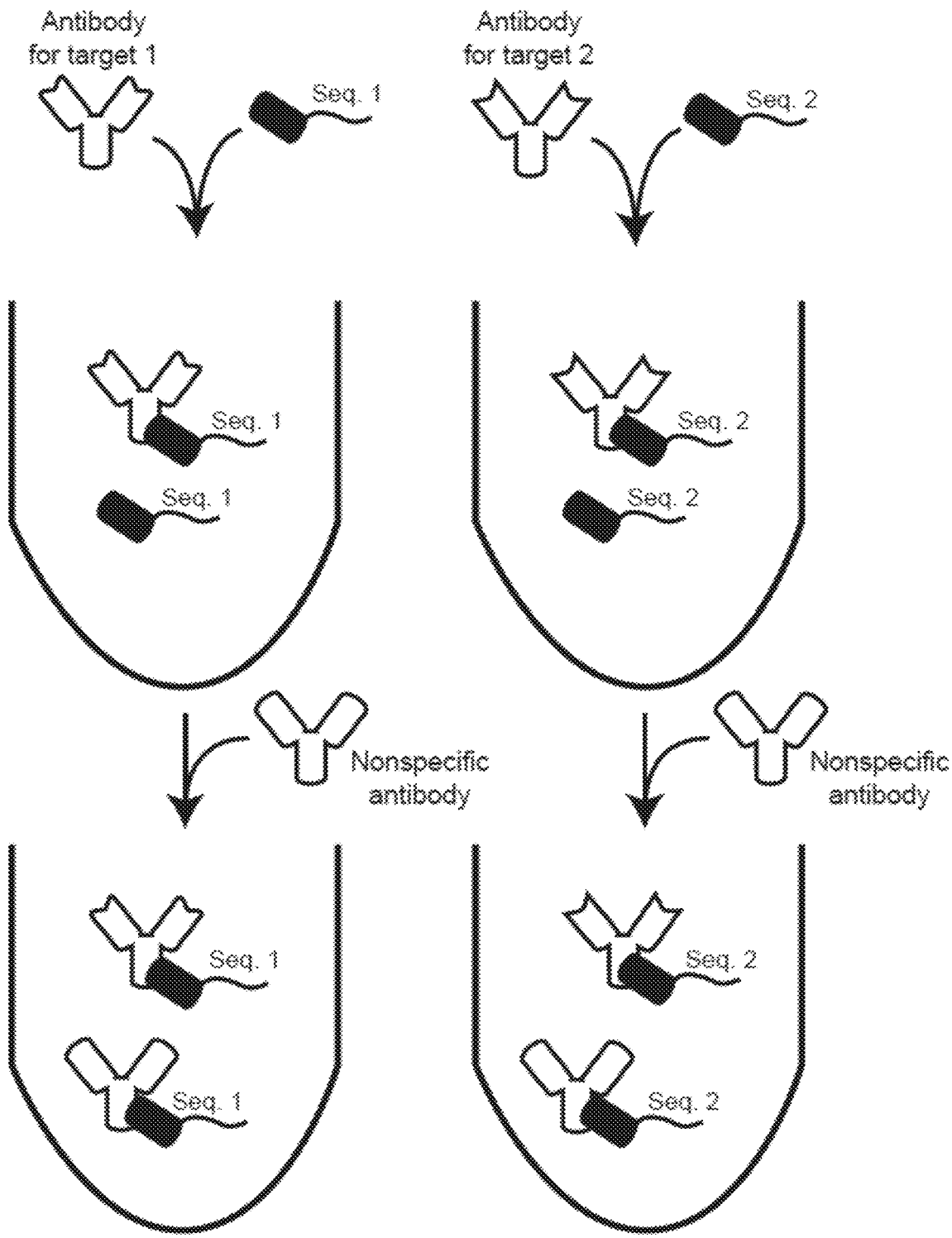
FIG. 2 shows one strategy to avoid purification in using MTAB-DMs. Nonspecific antibody has a flat shape on the binding end, with other features as described in FIG. 1.

In addition, the workflow shown in FIGS. 1 and 2 where one makes antibody:MTAB-DM complexes first and then stain the sample with the complexes (a strategy we hereby term '1-step staining'), one may also stain the sample with antibodies alone and then stain the sample using MTAB-DMs similar to the way secondary antibodies are used. We call this strategy '2-step staining'. In 2-step staining, if different MTAB-DMs are used to stain the sample simultaneously, one can ensure MTAB-DMs can specifically bind their respective intended antibodies and do not cross-bind. For example, one mouse primary antibody and one rabbit primary antibodies are used to stain the sample, then the anti-mouse Fab can be used as the MTAB of the MTAB-DM intended to bind the mouse primary antibody, and the anti-rabbit Fab can be used as the MTAB of the MTAB-DM intended to bind the rabbit primary antibody. If the primary antibodies are of different subtypes (e.g., IgG1, IgG2a, IgG2b, etc.), similar strategy can be used too.

Figure 4:
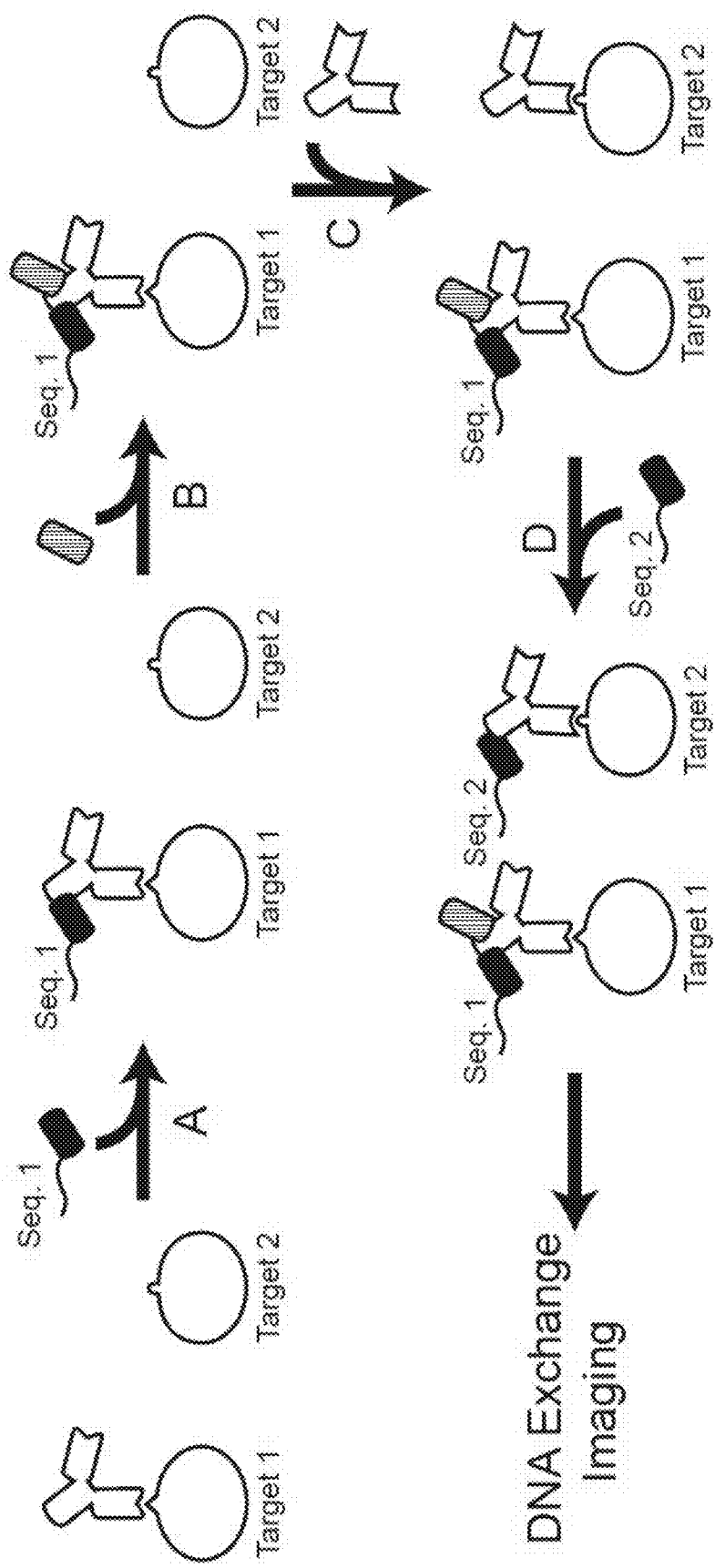
FIG. 4 shows an illustrative embodiment of DNA exchange imaging using 2-step staining and sequential staining.

If the primary antibodies are of the same subtype from the same organism, it may be impossible or impractical to find MTABs that can differentiate them. In this situation, one may still use the 2-step staining strategy but use the two primary antibodies sequentially. Using two antibodies of the same species and same isotype as an example, one implementation of such sequential staining workflow is shown in FIG. 4. First, the sample is stained with the first antibody, intended for the first target, followed by washes with PBS. Then (Step A) the sample is stained with MTAB-DM (e.g. Fab-oligonucleotide conjugate) intended for the first target, followed by washes in PBS. Then (Step B), the sample is treated with unlabeled MTAB (e.g., unmodified Fab, shown in gray rounded rectangles with black outline) that can occupy, if present, all unoccupied sites on the first primary antibody that may be bound by MTAB-DM intended for the second target that will be added later, followed by washes in PBS. Next (Step C), the sample is stained with the second primary antibody, intended for the second target, followed by washes with PBS. This step can be performed because the MTAB-DM intended for that first target and the unlabeled MTAB used earlier are both monovalent. If conventional secondary antibody were used instead of MTAB, the variable region unoccupied by the first primary antibody may bind the second primary antibody, causing false localization of the secondary antibody. Next (Step D), the sample is stained with the MTAB-DM intended for the second target. This MTAB-DM binds only binds the second primary antibody but not the first primary antibody because the available binding sites on the first primary antibody are already occupied by either the MTAB-DM intended for the first target, or the unlabeled MTAB introduced in Step B. If more targets are to be visualized, Steps B, C, D can be repeated with corresponding primary antibodies and MTAB-DMs.

It should be noted that the 1-step staining the 2-step staining can be performed for the same sample. For example, one may first introduce MTAB-DMs to one subset of targets using 1-step staining, then introduce MTAB-DMs to another subset of targets using 2-step staining, or vice versa.

EXAMPLES

Example 1

Demonstration that DNA-Conjugated Fab Fragments can be Used as MTAB-DM

In one embodiment of the technology described in this document, Fab fragment is used as the MTAB, and DNA oligonucleotide is used as the docking moiety. Two key questions regarding the feasibility of this embodiment are (a) whether the MTAB-DM:antibody complex can form fast enough, and (b) whether the MTAB-DM:antibody complex is stable enough for typical immunofluorescence applications. This example shows the procedure to answer this question and demonstrates that MTAB-DM produced by conjugating commercially available Fab fragments and amine-labeled DNA oligonucleotide can bind primary antibody quickly and form complexes that are stable enough. To create the MTAB-DM, we modified the goat anti-mouse-IgG Fab (Jackson ImmunoResearch Cat #115-007-003) with azido-(PEG)$_4$-NHS (Click Chemistry Tools, Cat #A103P-500) by mixing the two in PBS (where the final concentrations of the Fab fragment and azido-(PEG)$_4$-NHS were 1 mg/mL and 0.1 mM, respectively) for 1.5 hr followed by buffer exchange using a gel-filtration column. The azido-(PEG)$_4$-modified Fab fragment was then incubated with excess amount of 5'-DBCO-labeled oligonucleotide with the sequence: 5'-TCTGCTTTCCCG-3' (SEQ ID NO: 13) overnight to produce the Fab-DNA conjugate, which serves as the MTAB-docking moiety. Free DBCO-labeled DNA was removed by ultrafiltration with 30K molecular-weight cut-off. To facilitate the detection, this Fab-DNA conjugation was incubated with excess amount of 5'-ATTO488-labeled oligonucleotide with the sequence 5'-TCTGCTTTCCCGT-TATACATCTA-3' (SEQ ID NO: 12), followed by ultrafiltration with 30K molecular-weight cut-off to remove unbound ATTO488-labeled oligonucleotide (SEQ ID NO: 12), and quantified using UV spectrometry and spectrum linear unmixing We name the final complex "Fab-DNA: DNA-ATTO488".

Figure 5:
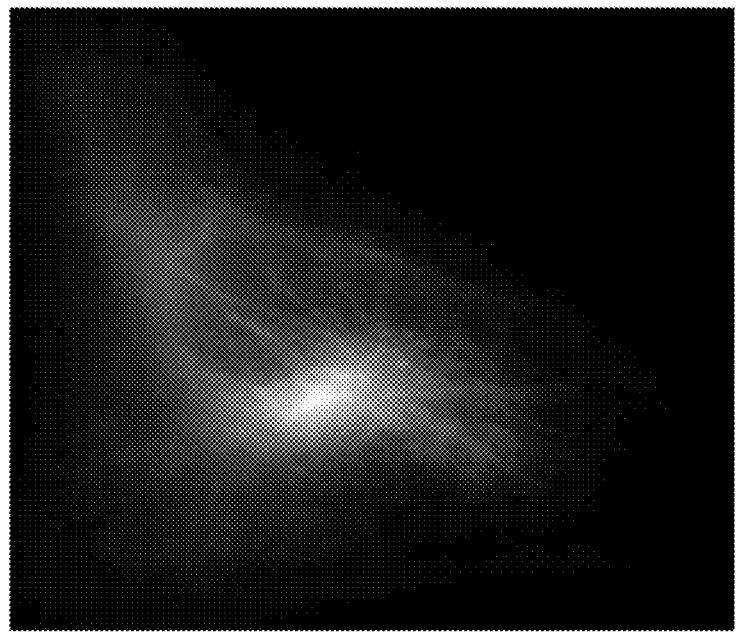
FIG. 5 corresponds to Example 1, showing the feasibility of using Fab as MTAB and DNA oligonucleotide as docking moiety.

We incubated 64.5 pmole Fab-DNA:DNA-ATTO488 with 1.5 microgram of mouse anti-alpha-tubulin antibody (clone DM1A) for 1.5 hr. Then 7.5 microliter of normal mouse serum was added to the mixture to provide target-nonspecific antibody to quench Fab-DNA:DNA-ATTO488 that are not bound to the primary antibody (i.e., mouse anti-alpha-tubulin antibody). Then 136 microliter of antibody dilution buffer (PBS with 1% BSA, 0.3% Triton-X 100, 5 uM (dT)$_{30}$ oligonucleotide) was added to the mixture. The final mixture was used to stain pre-fixed (using 3% paraformaldehyde and 0.1% glutaraldehyde for 10 min) and pre-blocked (with blocking buffer: PBS with 3% BSA+0.2% Triton X-100 for 1.5 hr) HeLa cells for overnight at 4° C. in a LabTek chamber. Then the HeLa cells were washed with PBS 4 times, 5 min each time, and imaged using the 488 nm laser and a FITC-channel filter cube. From the image shown in FIG. 5 it can be seen that microtubules are clearly stained, proving that (1) the 1.5 hr incubation was sufficient for the complex between the antibody and MTAB-DM (i.e., Fab- DNA:DNA-ATTO488) to form, and (2) during overnight incubation sufficient level of antibody:MTAB-DM complex remained intact.

Example 2

Lack of Exchange Between Antibody:MTAB-DM Complexes

To perform multiplexed immunofluorescence using the technology described here, one must ensure that during the experiment, the MTAB-DM intended to bind one primary antibody does not dissociate from the primary antibody (or the target-nonspecific antibody used to quench the MTAB-DM) and then bind to another primary antibody. This is especially important if multiple MTAB can bind multiple antibodies used in the sample. For example, if two rabbit primary antibodies of different target proteins are to be used (named here Antibody1 and Antibody2), and anti-rabbit Fab is used as MTAB for two MTAB-DM molecules (named here MTAB-DM1 and MTAB-DM2), one can complex Antibody1 and Antibody2 with MTAB-DM1 and MTAB-DM2, respectively. In this case, one must ensure that MTAB-DM1 does not bind Antibody2 during the experiment. This requires that MTAB must have high innate affinity for the antibodies so that the MTAB-DM:antibody complex does not dissociate too quickly during the experiment.

Figure 6A:
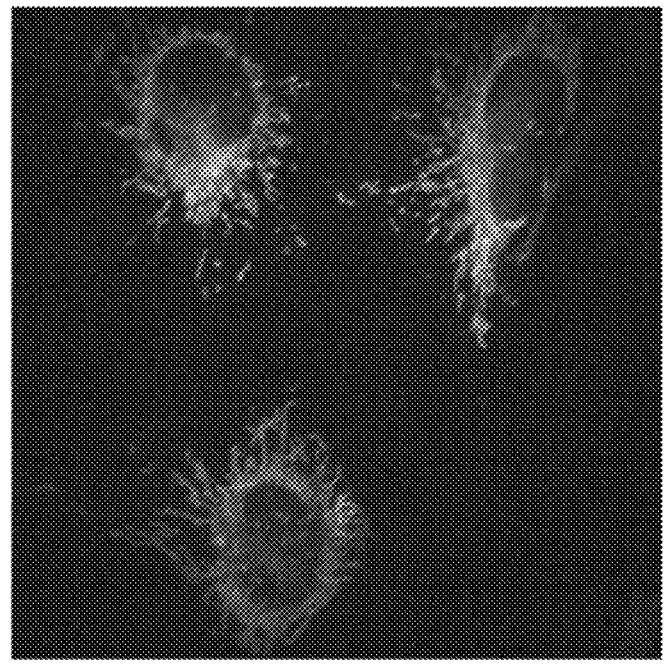
FIGS. 6A-B correspond to Example 2, providing an image of the FITC channel (A) and Cy5 channel (B) of HeLa cells stained with the Alexa488-labeled antibody:MTAB-DM complex targeting TOM20 (a mitochondria marker), and Alexa647-labeled antibody:MTAB-DM complex targeting lamin B (a nucleus membrane marker).
Figure 6B:
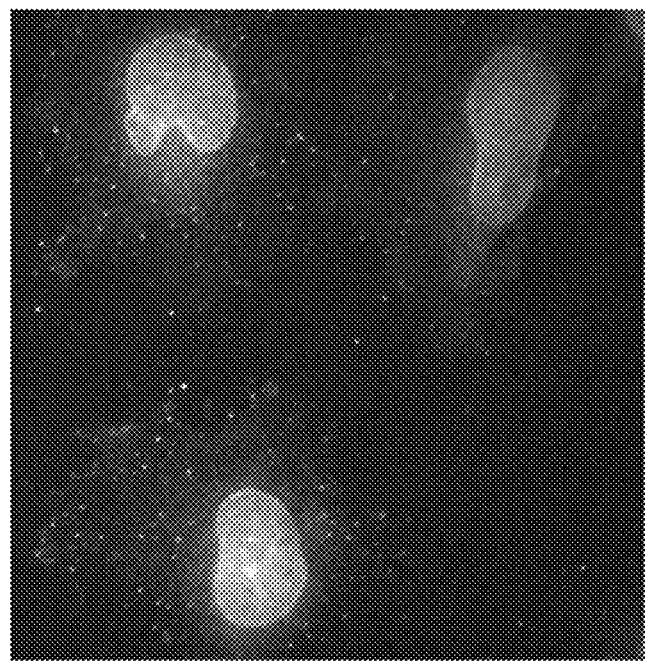

We used fluorescent-labeled Fab fragments as surrogates of MTAB-DMs to test whether Fab fragments have the innate affinity toward primary antibodies to achieve this desired behavior. To do this, we prepared two mixtures, named here Mixture1 and Mixture2. In Mixture 1, we mixed ~0.3 microgram of rabbit anti-TOM20 antibody (Santa Cruz Biotechnology, Cat #FL-145) and ~1.5 microgram of Alexa488-labeled goat anti-rabbit-Fc(IgG) Fab fragment for ~3 hrs in a final volume of 8 microliter. In Mixture 2, we mixed ~1.5 microgram of rabbit anti-lamin-B antibody (Abcam Cat #ab16048) and Alexa647-labeled goat anti-rabbit-Fc(IgG) Fab fragment for ~3 hrs in a final volume of 8 microliter. The buffer in both mixtures was PBS. Note that in both mixtures the primary antibodies have the host organism of rabbit. Next, 15 microliter of normal rabbit serum was added to each mixture. Next, 75 microliter of antibody dilution buffer (PBS with 1% BSA, 0.3% Triton-X 100, 5 uM $(dT)_{30}$ oligonucleotide) was added to each mixture. Next, the two mixtures were combined to stain pre-fixed (using 3% paraformaldehyde and 0.1% glutaraldehyde for 10 min) and pre-blocked (with blocking buffer: PBS with 3% BSA+0.2% Triton X-100 for 1.5 hr) HeLa cells for overnight at 4° C. in a LabTek chamber. Then the HeLa cells were washed with PBS 4 times, 5 min each time, and imaged using (a) 488 nm laser and a FITC-channel filter cube and (b) ~642 nm laser and a Cy5-channel filter cube. The images are shown in FIGS. 6A-B. It can be seen that in the FITC channel, where TOM20 (a mitochondria marker) is the intended target and is observable, no lamin B (a nucleus membrane marker) is observable, and that in the Cy5 channel, where lamin B is the intended target and is observable, no TOM20 is observable. Thus we can conclude that no exchange between antibody:MTAB-DM complexes was observed. In other words, Fab fragments have sufficient innate affinity toward primary antibodies.

Example 3

Evaluating MTAB-DM Binding to Target-Recognizing Antibody

The following protocol may be used to evaluate MTAB-DM binding to the target-recognizing antibody and to evaluate the extent to which MTAB-DM dissociates from the target-recognizing antibody.

(1) Stain the pre-fixed, pre-permeabilized, and pre-blocked (e.g., with BSA) sample with the pre-determined optimal concentration of primary antibody for X hours at a pre-determined optimal temperature, wherein X hours refers to the time the investigator plans to use for staining of the sample with the target-recognizing antibody.

(2) Wash the sample at room temperature with PBS for 4 times, 5 min each time.

(3) Stain the antibody with 100 nM of MTAB-DM at room temperature for 10 min.

(4) Wash the sample at room temperature with PBS for 4 times, 5 min each time.

(5) Stain the antibody with 100 nM of fluorescent-labeled Imager moiety at room temperature for 10 min.

(6) Wash the sample at room temperature with PBS for 4 times, 5 min each time.

(7) Image the sample and note down the imaging condition (light intensity, identity of filter cube, exposure time)

(8) Incubate the sample at temperature Temp-X for X hours, and then at temperature Temp-Y for Y hours, wherein Temp-X and X hours refers to the temperature and time the investigator plans to use for staining of the sample with the target-recognizing antibody and wherein Temp-Y for Y hours refers to the temperature and time after the antibody:MTAB-DM complexes are washed before the target is imaged.

(9) Image the sample again using the same imaging condition as in step (7).

(10) Quantify the fluorescence images, and compare fluorescence intensity of the same area in the images of step (7) and step (9).

Assuming no non-specific binding of MTAB-DM is seen, if the signal intensity of step (7) is substantially (e.g., >90%) lower than what is expected from standard immunofluorescence, or if the fluorescence intensity on image of step (9) is lower than that on image of step (7) by more than a desired percentage threshold (Z %), one can conclude that the affinity of MTAB-DM is too low. Otherwise one can conclude that the affinity of MTAB-DM is sufficiently high.

Example 4

Further Validation of the MTAB-DM

In addition to following the protocol in Example 3, one may further validate the MTAB-DM using the protocol in this Example to ensure that the binding of MTAB-DM does not cause the antibody to lose its ability to bind its target tightly.

(1) Mix 1.5 ug of the primary antibody with excess amount of MTAB-DM for 1 hour.

(2) Add excess amount of target-nonspecific antibodies to quench unbound MTAB-DM for 1 hour, and then dilute the mixture with PBS so that the volume is enough to cover the sample but is less than 150 uL.

(3) Apply the mixture to pre-fixed, pre-permeabilized, and pre-blocked sample and incubate at room temperature for X hours at temperature Temp-X. wherein Temp-X and X hours refers to the temperature and time the investigator plans to use for staining of the sample with the target-recognizing antibody.

(4) Wash the sample at room temperature with PBS for 4 times, 5 min each time;

(5) Apply 100 nM of the fluorescent-labeled Imager moiety to the sample and incubate for 10 min.

(6) Wash the sample at room temperature with PBS for 4 times, 5 min each time.

(7) Image the sample and note down the imaging condition (light intensity, identity of filter cube, exposure time)

(8) Incubate the sample at temperature Temp-Y for Y hours, wherein Temp-Y for Y hours refers to the temperature and time after the antibody:MTAB-DM complexes are washed before the target is imaged.

(9) Image the sample again using the same imaging condition as in step (7).

(10) Quantify the fluorescence images, and compare fluorescence intensity of the same area in the images of step (7) and step (9).

Assuming no non-specific binding of MTAB-DM is seen, if the signal intensity of step (7) is substantially (e.g., >90%) lower than what is expected from standard immunofluorescence, or if the fluorescence intensity on image of step (9) is lower than that on image of step (7) by more than a desired percentage threshold Z %, one can conclude that the affinity of MTAB-DM is too low or the MTAB-DM binding to the antibody causes to lose its ability to stably bind to its target—in either case the MTAB-DM may be disqualified. Otherwise one can conclude that the affinity of MTAB-DM is sufficiently high and the MTAB-DM can be used for this application.

Example 5

Embodiments

The following numbered items provide certain embodiments described herein.

Item 1. A method for exchange imaging of at least two targets in a sample comprising:
  a. providing at least two or more target-recognizing antibodies, each bound to a corresponding MTAB-DM reagent capable of binding monovalently to the target-recognizing antibodies
  b. incubating a sample with the two or more target-recognizing antibodies, each bound to a corresponding MTAB-DM reagent,
  c. applying at least two imager moieties corresponding to the MTAB-DM, either in series, in batches, or in parallel,
  d. imaging the at least two imager moieties either in series, in batches, or in parallel.

Item 2. The method of item 1, wherein the MTAB comprises Protein A, Protein G, Protein A/G, Protein L, or a monovalent antibody fragment.

Item 3. The method of any one of items 1-2, wherein the DMs (docking moieties) and the imager moieties comprise nucleic acids.

Item 4. The method of any one of items 1-3, wherein all of the target-recognizing antibodies each bound to a corresponding MTAB-DM reagent are incubated with the sample simultaneously.

Item 5. The method of any one of items 1-4, wherein all of the imager moieties are applied in series and the imaging occurs in series.

Item 6. The method of any one of items 1-4, wherein all of the imager moieties are applied in parallel and the imaging occurs in parallel.

Item 7. The method of any one of items 1-4, wherein the imager moieties are applied in batches with at least one batch having two or more imager moieties and the method having at least two batches and wherein the imaging occurs in at least two batches.

Item 8. The method of any one of items 1-8, wherein each imager moiety is labeled with a different observable moiety.

Item 9. The method of any one of items 1-5, wherein each imager moiety is labeled with the same observable moiety.

Item 10. The method of any one of items 1-5 or 7, wherein some of the imager moieties are labeled with the same observable moiety and some of the imager moieties are labeled with different observable moieties.

Item 11. The method of any one of items 1-10, wherein before incubating the target-recognizing antibodies with the sample, an excess of MTAB-DM is employed to prevent an excess of free target-recognizing antibody.

Item 12. The method of any one of items 1-11, wherein before incubating the target-recognizing antibodies with the sample, free MTAB-DM is removed using ultrafiltration or gel filtration.

Item 13. The method of any one of items 1-12, wherein nonspecific antibody is added to the staining, washing, and/or imaging buffer.

Item 14. The method of item 13, wherein the nonspecific antibody is an antibody from the same host species as the target recognizing antibodies.

Item 15. The method of item 14, wherein the nonspecific antibody is a polyclonal antibody found in normal serum (from an animal not immunized with any of the target proteins).

Item 16. The method of item 14, wherein the nonspecific antibody is a monoclonal antibody to a protein not present in the sample.

Item 17. The method of any one of items 1-16, wherein the imager moiety directly binds the docking moiety.

Item 18. The method of any one of items 1-17, wherein the imager moiety indirectly binds the docking moiety through an intermediate moiety.

Item 19. A composition comprising:
  a. an MTAB;
  b. a docking moiety covalently bound to the MTAB
  c. an intermediate moiety having a first domain and a second domain, wherein the first domain is capable of specifically binding to the docking moiety and wherein the second domain is not capable of specifically binding to the docking moiety.

Item 20. The composition of item 19, wherein the MTAB is Protein A, Protein G, Protein A/G, Protein L, or a monovalent antibody fragment.

Item 21. The composition of any one of items 19-20, wherein the docking moiety and the intermediate moiety comprise nucleic acids.

Item 22. The composition of item 21, wherein the docking moiety is from about 5 to 20 nucleic acids long, from about 8 to 15, or from about 10 to 12 nucleic acids long.

Item 23. The composition of any one of items 21 or 22, wherein the intermediate moiety is from about 10 to 40 nucleic acids long, from about 16 to 30, or from about 20 to 24 nucleic acids long.

Item 24. A method of making reagents for exchange imaging comprising:
 a. providing an MTAB;
 b. conjugating the MTAB to a docking moiety to form an MTAB-DM;
 c. providing a plurality of intermediate moieties, each having a first domain capable of specifically binding to the docking moiety and a second domain that is not capable of specifically binding to the docking moiety;
 d. combining the plurality of intermediate moieties with the MTAB-DM.

Item 25. The method of item 24, wherein the MTAB is Protein A, Protein G, Protein A/G, Protein L, or a monovalent antibody fragment.

Item 26. The method of any one of items 24-25, wherein the docking moiety and the intermediate moiety comprise nucleic acids.

Item 27. The method of item 26, wherein the docking moiety is from about 5 to 20 nucleic acids long, from about 8 to 15, or from about 10 to 12 nucleic acids long.

Item 28. The method of any one of items 26 or 27, wherein the intermediate moiety is from about 10 to 40 nucleic acids long, from about 16 to 30, or from about 20 to 24 nucleic acids long.

Item 29. The method of any one of items 24-28, wherein the plurality of intermediate moieties is combined with the MTAB-DM in a batch reaction.

Item 30. The method of any one of items 24-28, wherein the plurality of intermediate moieties is combined with the MTAB-DM separately.

Item 31. A kit for exchange imaging of at least two targets in a sample comprising
 a. at least two different MTAB-DM reagents comprising a MTAB and a docking moiety capable of specifically binding an imager moiety;
 b. optionally at least two different target-recognizing antibodies;
 c. at least two imager moieties labeled with observable moieties and capable of specifically binding to the MTAB-DM reagents, respectively,
 d. optionally at least one antibody that does not specifically bind to any of the targets.

Item 32. The kit of item 31, wherein the MTAB is chosen from Protein A, Protein G, Protein A/G, Protein L, or a monovalent fragment of an antibody.

Item 33. The kit of any one of items 31-32, wherein the docking moiety is a nucleic acid docking moiety and the imager moiety is nucleic acid imager moiety.

Item 34. The kit of any one of items 32-33, wherein the docking moiety is a protein, peptide, or chemical compound and the imager moiety is a complementary protein, peptide, or chemical compound.

Item 35. The kit of item 34, wherein the docking moiety and imager moiety are streptavidin and biotin, respectively in either order.

Item 36. The kit of any one of items 31-35, wherein the MTAB and docking moiety are conjugated by using streptavidin or conjugation docking moieties such as SNAP-tag®, CLIP-tag™, HaloTag®, and AviTag™

Item 37. The kit of any one of items 31-36, wherein the MTAB-DM is capable of binding at least two different target-recognizing antibodies with an affinity of from about 1 fM to 1 nM.

Item 38. The kit of any one of items 31-37, wherein the observable moiety is an optically observable moiety.

Item 39. The kit of item 38, wherein the observable moiety is a P-dot, a fluorescent protein, a fluorescent nucleic acid, a Q-dot, a nanoparticle, or a SERS reporter.

Item 40. A method for exchange imaging employing the reagents of any one of items 19-23 or 31-39.

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

All of the documents cited herein are incorporated by reference in their entirety for the information for which they are cited.

What is claimed is:

1. A method for exchange imaging of at least two targets in a sample comprising:
    (a) incubating a sample with at least two or more target-recognizing antibodies, each bound to a corresponding monovalent tight antibody binder-docking moiety (MTAB-DM) wherein the MTAB comprises Protein A, Protein G, Protein A/G, Protein L, or a monovalent antibody fragment, capable of binding monovalently to the target-recognizing antibodies, and the DM comprising a single-stranded nucleic acid is covalently bound to the MTAB;
    (b) applying at least two imager moieties each capable of specifically binding to the docking moiety of the corresponding MTAB-DM, either in series, in batches, or in parallel;
    (c) imaging the at least two imager moieties either in series, in batches, or in parallel, wherein at least one nonspecific antibody that does not specifically bind to any of the targets is added to a buffer used in the incubating, applying, or imaging.

2. The method of claim 1, wherein all of the target-recognizing antibodies each bound to a corresponding MTAB-DM reagent are incubated with the sample simultaneously.

3. The method of claim 1, wherein the imager moieties are applied in batches with at least one batch having two or more imager moieties and the method having at least two batches and wherein the imaging occurs in at least two batches.

4. The method of claim 1, wherein before incubating the target-recognizing antibodies with the sample, an excess of MTAB-DM is employed to prevent an excess of free target-recognizing antibody.

5. The method of claim 1, wherein before incubating the target-recognizing antibodies with the sample, free MTAB-DM is removed using ultrafiltration or gel filtration.

6. The method of claim 1, wherein the nonspecific antibody is an antibody from the same host species as the target recognizing antibodies.

7. The method of claim 6, wherein the nonspecific antibody is a polyclonal antibody found in normal serum from an animal not immunized with any of the target proteins.

8. The method of claim 6, wherein the nonspecific antibody is a monoclonal antibody to a protein not present in the sample.

9. A kit for exchange imaging of at least two targets in a sample comprising
    (a) at least two different MTAB-DM reagents, each MTAB-DM reagent comprising a MTAB comprising Protein A, Protein G, Protein A/G, Protein L, or a monovalent antibody fragment, being monovalently bound to a target-recognizing antibody, and a docking moiety comprising a single-stranded nucleic acid being covalently bound to the MTAB, wherein the docking moiety is capable of specifically binding an imager moiety directly or indirectly via an intermediate moiety, each intermediate moiety having a first domain capable of specifically binding to the docking moiety and a second domain that is not capable of specifically binding to the docking moiety;
- (b) at least two imager moieties labeled with observable moieties and capable of specifically binding directly, or indirectly via the intermediate moiety, to the docking moiety of the MTAB-DM reagents, respectively; and
- (c) at least one nonspecific antibody that does not specifically bind to any of the targets.

10. The kit of claim 9, wherein the MTAB-DM is capable of binding at least two different target-recognizing antibodies with an affinity of from about 1 fM to 1 nM.

11. A method for exchange imaging employing the reagents of claim 9.

12. A method for exchange imaging of at least two targets in a sample comprising:
- (a) incubating a sample with a first target-recognizing antibody;
- (b) incubating the sample with an MTAB-DM corresponding to the first target-recognizing antibody, wherein the MTAB comprises Protein A, Protein G, Protein A/G, Protein L, or a monovalent antibody fragment, capable of binding monovalently to the target-recognizing antibodies, and the DM is covalently bound to the MTAB and comprises a single-stranded nucleic acid;
- (c) incubating the sample with an unlabeled MTAB, not bound to any DM and capable of binding to an unoccupied site on the first target-recognizing antibody;
- (d) incubating the sample with a second target-recognizing antibody;
- (e) incubating the sample with an MTAB-DM corresponding to the second target-recognizing antibody;
- (f) optionally if more than two targets are being imaged, repeating steps c-e;
- (g) applying at least two imager moieties each capable of specifically binding the DM of the corresponding MTAB-DM, either in series, in batches, or in parallel;
- (h) imaging the at least two imager moieties either in series, in batches, or in parallel.

13. The method of claim 12, wherein steps a and b are performed simultaneously by incubating the sample with a mixture of the first target-recognizing antibody and the corresponding MTAB-DM simultaneously.

14. The method of claim 12, wherein steps d and e are performed simultaneously by incubating the sample with a mixture of the second target-recognizing antibody and the corresponding MTAB-DM simultaneously.

15. The method of claim 12, wherein the imager moieties are applied in batches with at least one batch having two or more imager moieties and the method having at least two batches and wherein the imaging occurs in at least two batches.

16. The method of claim 1, further comprising washing with a buffer comprising at least one nonspecific antibody that does not specifically bind to any of the targets after the incubating, applying, or imaging.

* * * * *